United States Patent
Leak et al.

(10) Patent No.: US 12,290,293 B2
(45) Date of Patent: *May 6, 2025

(54) BONE FIXATION SYSTEMS, APPARATUSES, AND METHODS WITH ANTI-BACK-OUT FEATURE

(71) Applicant: Leith Medical LLC, Austin, TX (US)

(72) Inventors: Timothy J. Leak, Austin, TX (US); Thomas G. Smith, Austin, TX (US)

(73) Assignee: LEITH MEDICAL, LLC, Buda, TX (US)

( * ) Notice: Subject to any disclaimer, the term of this patent is extended or adjusted under 35 U.S.C. 154(b) by 261 days.

This patent is subject to a terminal disclaimer.

(21) Appl. No.: 18/172,842

(22) Filed: Feb. 22, 2023

(65) Prior Publication Data

US 2023/0200868 A1 Jun. 29, 2023

Related U.S. Application Data

(63) Continuation of application No. 16/921,288, filed on Jul. 6, 2020, now Pat. No. 11,617,605, which is a
(Continued)

(51) Int. Cl.
*A61B 17/80* (2006.01)
*A61B 17/86* (2006.01)

(52) U.S. Cl.
CPC ...... *A61B 17/8047* (2013.01); *A61B 17/8042* (2013.01); *A61B 17/8052* (2013.01); *A61B 17/8625* (2013.01); *A61B 17/863* (2013.01)

(58) Field of Classification Search
CPC .................. A61B 17/8047; A61B 17/8042
See application file for complete search history.

(56) References Cited

U.S. PATENT DOCUMENTS 5,364,399 A * 11/1994 Lowery .............. A61B 17/1728
606/295
5,370,646 A 12/1994 Reese
(Continued)

FOREIGN PATENT DOCUMENTS

WO 2007/056516 A2 5/2007
WO 2014/062690 A1 4/2014
(Continued)

OTHER PUBLICATIONS

U.S. Appl. No. 17/068,920, filed Oct. 13, 2020 (IFW).
(Continued)

*Primary Examiner* — Christian A Sevilla
(74) *Attorney, Agent, or Firm* — Slayden Grubert Beard PLLC

(57) ABSTRACT

A locking clip for retaining a fastener in a bone fixation plate, the locking clip comprising a flexure member and a body member coupled to the flexure member, the body member comprising a locking tab, the locking tab configured to provide an axial limitation to motion of the fastener in a non-rotationally-ratcheting manner, the flexure member resiliently flexible to permit displacement of the locking tab to allow passage of a fastener head of the fastener, the locking tab configured to translate a downward force of the fastener head into a lateral spreading force to effect the displacement, the body member defining a clip tool engagement cavity for translational displacement of the locking tab.

15 Claims, 35 Drawing Sheets

Related U.S. Application Data continuation of application No. 16/134,760, filed on Sep. 18, 2018, now Pat. No. 10,736,679, which is a continuation of application No. 15/478,036, filed on Apr. 3, 2017, now Pat. No. 10,105,169, which is a continuation-in-part of application No. 15/040,339, filed on Feb. 10, 2016, now abandoned.

(60) Provisional application No. 62/386,502, filed on Dec. 3, 2015, provisional application No. 62/285,940, filed on Nov. 13, 2015.

(56) References Cited

U.S. PATENT DOCUMENTS

| | | | |
|---|---|---|---|
| 5,501,684 | A | 3/1996 | Schlapfer |
| 5,520,690 | A | 5/1996 | Errico |
| 5,578,034 | A | 11/1996 | Estes |
| 5,902,303 | A | 5/1999 | Eckhof |
| 5,954,722 | A | 9/1999 | Bono |
| 6,139,550 | A * | 10/2000 | Michelson .............. A61B 17/80 606/295 |
| 6,152,927 | A * | 11/2000 | Farris ................. A61B 17/8033 606/295 |
| 6,235,033 | B1 | 5/2001 | Brace |
| 6,241,731 | B1 | 6/2001 | Fiz |
| 6,261,291 | B1 * | 7/2001 | Talaber .................. A61B 17/80 606/295 |
| 6,599,290 | B2 | 7/2003 | Bailey |
| 6,602,255 | B1 * | 8/2003 | Campbell .......... A61B 17/8042 606/76 |
| 6,884,242 | B2 | 4/2005 | LeHuec |
| 7,001,389 | B1 | 2/2006 | Navarro |
| D603,510 | S | 11/2009 | Kriska |
| 7,766,917 | B2 | 8/2010 | Kugler |
| 7,766,947 | B2 | 8/2010 | Hawkes |
| 7,963,982 | B2 | 6/2011 | Kirschman |
| 7,981,140 | B2 | 7/2011 | Burkhart |
| 8,012,174 | B2 | 9/2011 | ElAttrache et al. |
| 8,100,955 | B2 | 1/2012 | Blain |
| 8,202,296 | B2 | 6/2012 | Burkhart |
| 8,202,297 | B2 | 6/2012 | Burkhart |
| 8,231,653 | B2 | 7/2012 | Dreyfuss |
| 8,348,975 | B2 | 1/2013 | Dreyfuss |
| 8,388,665 | B2 | 3/2013 | Eberlein |
| 8,465,522 | B2 | 6/2013 | Burkhart |
| 8,506,607 | B2 | 8/2013 | Eckhof et al. |
| 8,562,656 | B2 | 10/2013 | Humphreys |
| 8,591,578 | B2 | 11/2013 | Albertorio et al. |
| 8,628,573 | B2 | 1/2014 | Roller et al. |
| 8,663,279 | B2 | 3/2014 | Burkhart et al. |
| 8,784,459 | B2 | 7/2014 | Kaufman et al. |
| 8,858,560 | B2 | 10/2014 | Bradley et al. |
| 8,961,569 | B2 | 2/2015 | Kaufman et al. |
| 8,986,346 | B2 | 3/2015 | Dreyfuss |
| 9,044,273 | B2 | 6/2015 | Richelsoph |
| 9,107,653 | B2 | 8/2015 | Sullivan |
| 9,113,859 | B2 | 8/2015 | Dooney, Jr et al. |
| 9,179,950 | B2 | 11/2015 | Zajac et al. |
| 9,204,960 | B2 | 12/2015 | Albertorio et al. |
| 9,326,844 | B2 | 5/2016 | Schmieding et al. |
| 9,332,979 | B2 | 5/2016 | Sullivan |
| 9,345,471 | B2 | 5/2016 | Sullivan |
| 9,421,086 | B2 | 8/2016 | Roller et al. |
| 9,463,011 | B2 | 10/2016 | Dreyfuss et al. |
| 9,504,462 | B2 | 11/2016 | Dixler et al. |
| 9,526,489 | B2 | 12/2016 | Burkhart |
| 9,615,821 | B2 | 4/2017 | Sullivan |
| 9,642,610 | B2 | 5/2017 | Albertorio et al. |
| 9,687,222 | B2 | 6/2017 | Dreyfuss et al. |
| 9,693,765 | B2 | 7/2017 | Sullivan et al. |
| 9,737,292 | B2 | 8/2017 | Sullivan et al. |
| 9,801,621 | B2 | 10/2017 | Benavitz |
| 9,855,029 | B2 | 1/2018 | Sullivan |
| 9,867,607 | B2 | 1/2018 | Sullivan |
| 9,913,672 | B2 | 3/2018 | Kaufmann |
| 10,076,407 | B2 | 9/2018 | Albertorio et al. |
| 10,085,739 | B2 | 10/2018 | Dooney, Jr et al. |
| 10,105,169 | B2 | 10/2018 | Leak et al. |
| 10,172,606 | B2 | 1/2019 | Sullivan et al. |
| 10,172,607 | B2 | 1/2019 | Burkhart |
| 10,206,670 | B2 | 2/2019 | Thornes |
| 10,245,016 | B2 | 4/2019 | Zajac et al. |
| 10,251,686 | B2 | 4/2019 | Zajac et al. |
| 10,265,060 | B2 | 4/2019 | Dooney, Jr. et al. |
| 10,285,801 | B2 | 5/2019 | Roller et al. |
| 10,335,136 | B2 | 7/2019 | Dooney, Jr et al. |
| 10,368,855 | B2 | 8/2019 | Burkhart |
| 10,398,426 | B2 | 9/2019 | Burkhart et al. |
| 10,441,408 | B2 | 10/2019 | Dreyfuss et al. |
| 10,448,943 | B2 | 10/2019 | Guerra et al. |
| 10,492,776 | B2 | 12/2019 | Dreyfuss et al. |
| RE47,811 | E | 1/2020 | Sullivan et al. |
| 10,524,775 | B2 | 1/2020 | Benedict et al. |
| 10,568,733 | B2 | 2/2020 | Park et al. |
| 10,575,842 | B2 | 3/2020 | Lund |
| 10,646,327 | B2 | 5/2020 | Lund |
| 10,736,620 | B2 | 8/2020 | Dreyfuss et al. |
| 10,736,679 | B2 | 8/2020 | Leak et al. |
| 2001/0047172 | A1 | 11/2001 | Foley |
| 2002/0019634 | A1 | 2/2002 | Bonutti |
| 2002/0188297 | A1 | 12/2002 | Dakin |
| 2003/0225409 | A1 | 12/2003 | Freid |
| 2004/0019353 | A1 | 1/2004 | Freid |
| 2004/0127900 | A1 | 7/2004 | Konieczynski |
| 2006/0009770 | A1 | 1/2006 | Speirs |
| 2006/0264944 | A1 | 11/2006 | Cole |
| 2007/0244489 | A1 | 10/2007 | Patel |
| 2008/0147127 | A1 | 6/2008 | Tipimeni |
| 2008/0287999 | A1 | 11/2008 | Markworth |
| 2011/0034925 | A1 | 2/2011 | Tipirneni |
| 2011/0172666 | A1 | 7/2011 | Heilman |
| 2013/0123841 | A1 | 5/2013 | Lyon |
| 2013/0190825 | A1 | 7/2013 | Perrow |
| 2015/0094764 | A1 | 4/2015 | Konieczynski |
| 2015/0245859 | A1 | 9/2015 | McMillen |
| 2015/0359574 | A1 | 12/2015 | Black |
| 2016/0081730 | A1 | 3/2016 | Black et al. |
| 2016/0213368 | A1 | 7/2016 | Stecco |
| 2016/0220286 | A1 | 8/2016 | Garvey et al. |
| 2016/0317203 | A1 | 11/2016 | Weiman et al. |
| 2016/0317318 | A1 | 11/2016 | Carlson et al. |
| 2017/0209140 | A1 | 4/2017 | Thornes |
| 2017/0156767 | A1 | 6/2017 | Chaudot et al. |
| 2017/0156771 | A1 | 6/2017 | Brinker |
| 2019/0133655 | A1 | 5/2019 | Bonutti |
| 2020/0330140 | A1 | 10/2020 | Leak et al. |
| 2021/0106367 | A1 | 4/2021 | Leak |
| 2021/0106369 | A1 | 4/2021 | Leak |

FOREIGN PATENT DOCUMENTS

| | | |
|---|---|---|
| WO | 2014/089534 | 6/2014 |
| WO | 2016/070191 | 5/2016 |
| WO | 2017/196769 | 11/2017 |

OTHER PUBLICATIONS

International Search Report and Written Opinion of International Application No. PCT/US2020/055303, mailing date: Feb. 19, 2021, 21 pages.

International Preliminary Report of International Application No. PCT/US2020/055303, mailing date Apr. 28, 2022, 10 pages.

International Preliminary Report and Written Opinion of International Application No. PCT/US2020/055302, mailing date Apr. 28, 2022, 9 pages.

International Search Report and Written Opinion of International Application No. PCT/US2020/055302, mailing date: Feb. 10, 2021, 21 pages.

* cited by examiner

BONE FIXATION SYSTEMS, APPARATUSES, AND METHODS WITH ANTI-BACK-OUT FEATURE

CROSS-REFERENCE TO RELATED APPLICATION(S)

The present application is a continuation of U.S. patent application Ser. No. 16/921,288, filed on Jul. 6, 2020, which is a continuation of U.S. patent application Ser. No. 16/134,760, filed on Sep. 18, 2018, now U.S. Pat. No. 10,736,679 granted Aug. 11, 2020, which is a continuation of U.S. patent application Ser. No. 15/478,036, filed on Apr. 3, 2017, now U.S. Pat. No. 10,105,169 granted Oct. 23, 2018, which is a continuation-in-part of U.S. patent application Ser. No. 15/040,339, filed on Feb. 10, 2016, which claims priority to U.S. Provisional Patent Application No. 62/285,940, filed on Nov. 13, 2015, and to U.S. Provisional Patent Application No. 62/386,502, filed on Dec. 3, 2015, the contents of each of these applications are incorporated herein by reference in entirety.

BACKGROUND

Field of the Disclosure

This disclosure relates generally to orthopedic devices, and more specifically, to a bone fixation system, apparatus, and method with anti-back out feature.

Background of the Disclosure

For various bone fractures, the use of orthopedic plates is a well-known technique to stabilize the bone as needed for proper healing. Generally, a rigid, often metal plate is placed on the outer surface of the bone across the fracture, and orthopedic screws extend through the plate into the bone on either side of the fracture. The plate offers support and stability to the bone during the healing period. Typically, the orthopedic screws have threads along a shaft, which are adapted to engage bone. The head portion of the screw is commonly a standard screw head that provides a compressive force as the screw is threaded into the bone, thereby compressing the orthopedic plate against the bone.

It may also be necessary to secure and stabilize the cervical vertebrae during spinal fusion surgeries. Stabilization of the cervical vertebrae facilitates an appropriate healing or a preferred result. In such situations, an orthopedic plate may be mounted on one or more vertebrae during the surgery using orthopedic screws. The plates are firmly secured to the spinal column so that the plates are not broken when stressed. Typically, screws are used to mount the cervical plate to the one or more vertebrae.

The term "micromotion" refers to microscopic relative displacements of a loaded intraosseously implanted orthopedic hardware component with respect to the bone surrounding it. Micromotion between the bone and the portion of the orthopedic screws within the bone or vertebrae can cause loosening of one or more orthopedic screws, often called back out. When screw back out occurs, loosening of the entire assembly occurs, thereby diminishing the stability of the set fracture or spinal fusion.

To address screw back out, some orthopedic systems have used screws with threaded heads. In such systems, the head of the screw threadably engages in threads in the orthopedic plate to lock the screws relative to the plate. These systems, however, do not provide the necessary control of compression between the plate and bone because the screw is locked relative to the plate. Accordingly, this type of system provides sub-optimal stability for attachment of orthopedic plates to bone(s). In addition, the threaded engagement between the screw and plate can loosen over time.

Other systems use secondary discrete hardware to lock a bone screw to the plate. For example, some systems use a set screw that sets against the head of the orthopedic screw to prevent back out of the screw. In another system, a washer and screw assembly is used in combination to provide compression against the head of the orthopedic screw and prevent back out. Such systems increase the number of individual hardware pieces for a given application, increasing not only the complexity of installing an orthopedic plate, but also the chances of an object being lost in the surgical wound.

BRIEF DESCRIPTION OF THE DRAWINGS

The present disclosure may be better understood, and its numerous features and advantages made apparent to those skilled in the art by referencing the accompanying drawings. Embodiments are illustrated by way of example and are not limited by the accompanying figures.

The use of the same reference symbols in different drawings indicates similar or identical items. Items in the figures are illustrated for simplicity and clarity and have not necessarily been drawn to scale.

DETAILED DESCRIPTION OF THE DRAWINGS

Embodiments of systems, apparatuses, and methods for bone fixation with an anti-back feature are described. In an embodiment, an orthopedic plate with embedded clamps that set on the head of orthopedic screws can be used to provide stability to a bone or bones, with the clamps preventing the back out of the orthopedic screws. Because the screws need not be fixed relative to the plate, the bone fixation system can obtain the desired compression for stability. In addition, because the clamps have at least one protrusion that sits on a portion of the head of the orthopedic screws, the bone fixation system prevents back out of the screws. Furthermore, because the clamps can be, as examples, either embedded within or placed in a notch and channel in the sidewall of the screw holes before the operation begins, the number of individual hardware pieces remains limited as does the complexity of installing the bone fixation system.

In another embodiment, the configuration of the screw holes in the orthopedic plate and the head of the orthopedic screws allow the screws to be inserted perpendicularly to the bone or at angle. Such configuration allows the bone fixation system to provide traction or lateral forces in addition to the desired compression.

Figure 1:
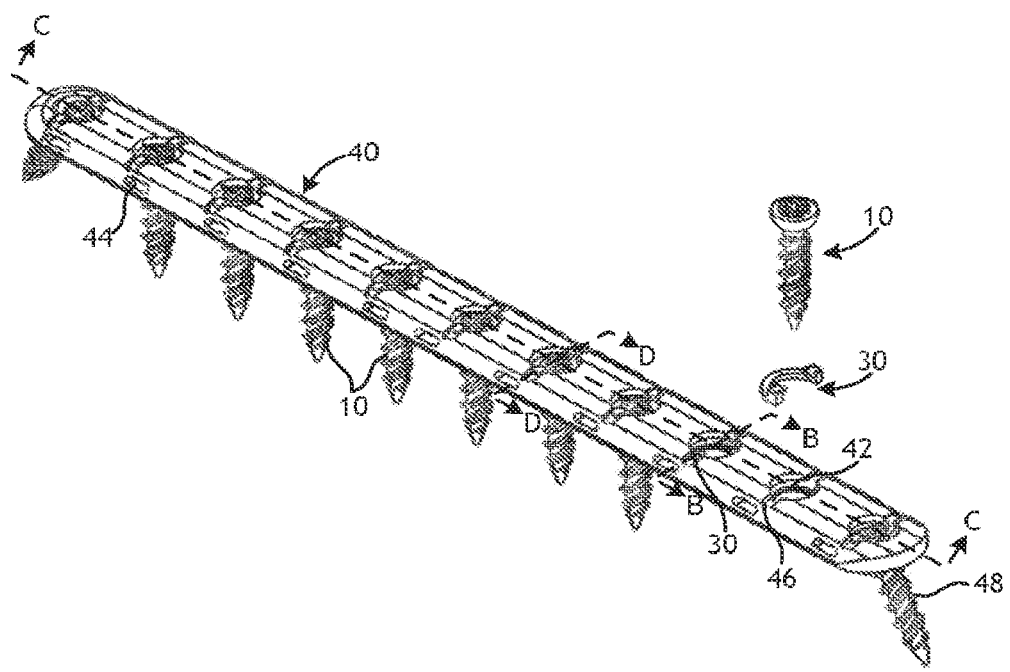
FIG. 1 is a perspective view illustrating one embodiment of the bone fixation system with an anti-back out feature including an orthopedic plate, clamp, and screw.

FIG. 1 is a perspective view illustrating one embodiment of the bone fixation system with an anti-back out feature including an orthopedic plate, clamp, and screw. The orthopedic plate 40 can be any orthopedic plate which has application in providing compression or other stabilization to bone, including but not limited to, plates for fractures of the diaphysis and/or metaphysis of long bones, plates for placement on the mandible or other portions of the skull, plates for osteosynthesis, particularly along the vertebrae, and plates for placement on a bone or bones in the foot, ankle, shoulder, hand, and/or wrist. Those skilled in the art would understand that the orthopedic plate 40 may be shaped for placement on many different types of bones and is not limited to the illustrative examples provided. The plate generally includes a plurality of screw holes, one such screw hole 42 is shown in FIG. 1. The screw hole 42 may be threadless and in an embodiment of the bone fixation system with anti-back out feature includes a notch and channel 46 in the sidewall of the hole. The semi-circle-shaped clamp 30 sits within the notch and channel 46. The orthopedic plate 40 may also include openings 44 that allow for visualization of the bone once the plate 40 is inserted. A plurality of orthopedic screws 10, 48 can be driven into the bone through the plurality of screw holes 42. While eleven orthopedic screws 10, 48 are illustrated in FIG. 1, those skilled in the art would understand that the bone plate 40 may include more or less than eleven orthopedic screws 10, 48.

Figure 2:
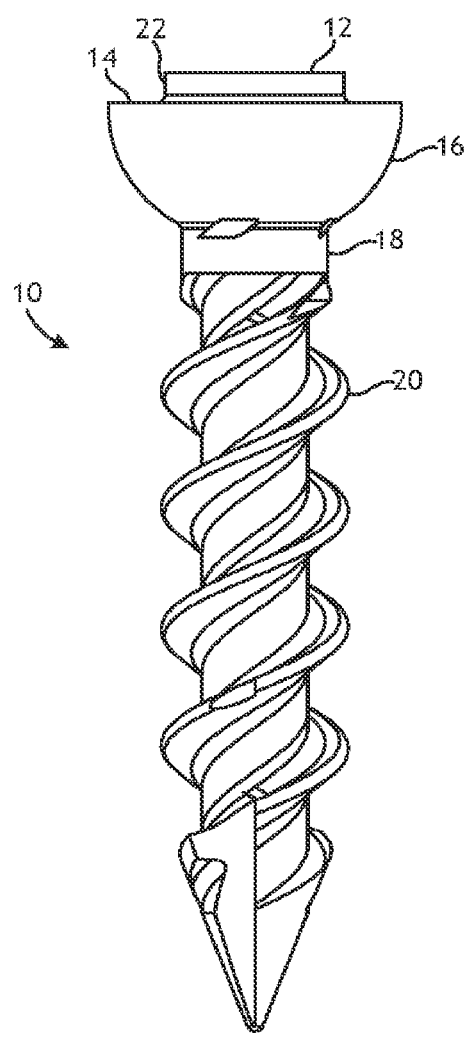
FIG. 2 is a side view illustrating one embodiment of an orthopedic screw used in a bone fixation system with an anti-back out feature.

FIG. 2 is a side view illustrating one embodiment of an orthopedic screw used in a bone fixation system with an anti-back out feature. The orthopedic screw 10 includes a head with an upper recess (not shown) on surface 12, for example, a hex slot, for a driver, a shaft 18 with bone engaging threads 20, and a conical taper 16 at the lower end of the head leading into the shaft 18. The head includes a cylindrical portion 22 with a radius that is less than the radius of the head. As a result, a portion of the clamp 30 (not shown in FIG. 2) can rest on a portion of surface 14.

While the embodiment illustrated in FIG. 2 is a fully threaded cancellous screw, other embodiments may be practiced. As examples, embodiments may be practiced as a partially threaded cancellous screw, a fully threaded cortical screw, a partially threaded cortical screw, a cancellous and cortical screw, and others. Fully threaded screws have threads over substantially the entire length of their shafts, while partially threaded screws have threads over a portion of the length of their shafts, with at least another portion of the length of their shafts unthreaded. A cancellous and cortical screw has threads of one type along a distal portion of its shaft and threads of another type along a proximal portion of its shaft. The distal portion may be immediately adjacent to the proximal portion, or the distal portion and the proximal portion may be separated from each other, for example, by an unthreaded portion. Illustrations of examples of orthopedic screws in accordance with other embodiments may be found in FIGS. 25-27, which are described further below.

Figure 3:
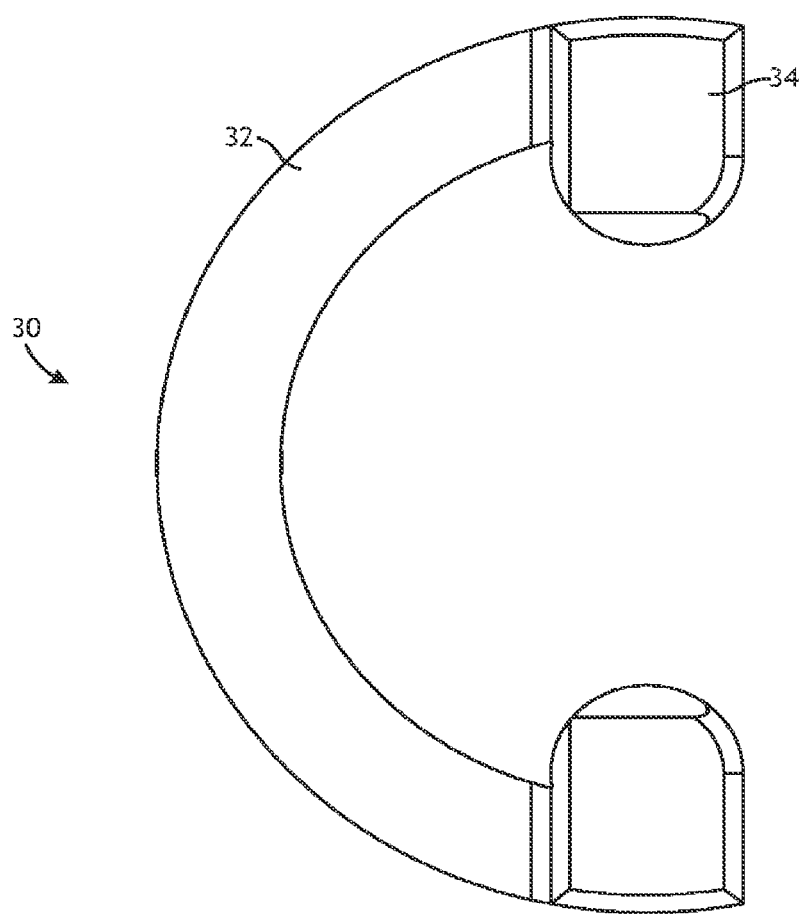
FIG. 3 is a top view illustrating one embodiment of a clamp used in a bone fixation system with an anti-back out feature.
Figure 4:
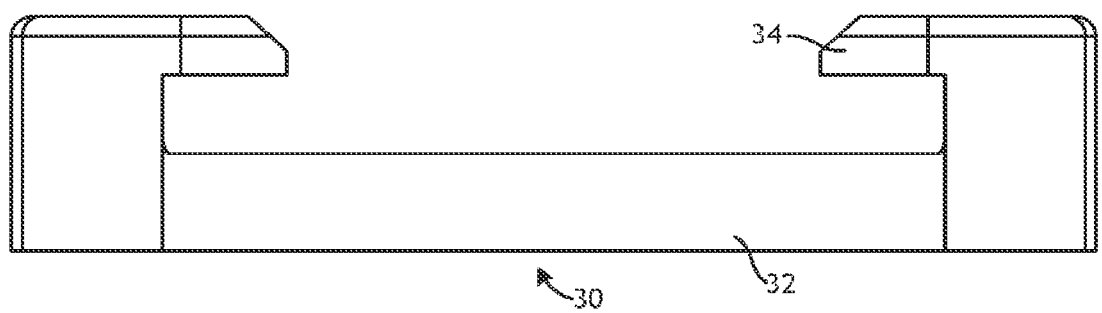
FIG. 4 is an elevation view of one embodiment of a clamp used in a bone fixation system with an anti-back out feature.

FIG. 3 is a top view illustrating one embodiment of a clamp used in a bone fixation system with an anti-back out feature. The clamp 30 includes a substantially semi-circle-shaped washer 32 with two protrusions 34 extending vertically away from the washer 32 and toward the center of the washer 32. FIG. 4 is an elevation view of this embodiment of a clamp 30 of FIG. 3, showing a profile of the washer 32 and protrusions 34.

Figure 5:
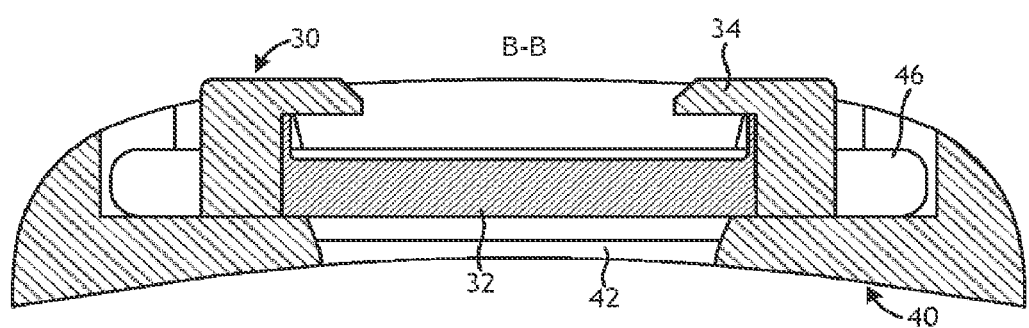
FIG. 5 is a cross-section of one embodiment of an orthopedic plate and clamp assembly used in a bone fixation system with an anti-back out feature taken along line B-B.

FIG. 5 is a cross-section of one embodiment of an orthopedic plate and clamp assembly used in a bone fixation system with an anti-back out feature taken along line B-B of FIG. 1. Clamp 30 sits within the notch and channel 46 of the hole 42 in the orthopedic plate 40. The washer portion 32 of the clamp 30 sits on the surface of the notch and channel 46. The protrusions 34 of the clamp 30 may be substantially flat with the top surface of the plate 40. The curved structure of the lower surface of the plate 40 complements the natural curved structure of a bone.

Figure 6A:
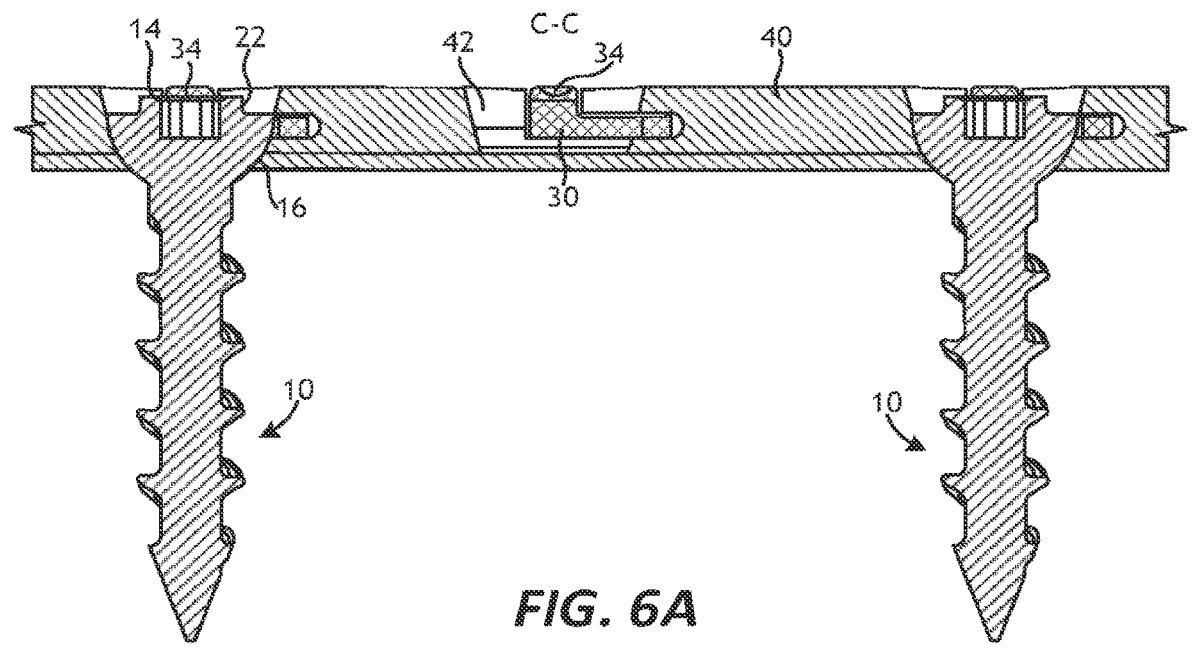
FIG. 6A is a cross-section of one embodiment of an orthopedic plate, clamp, and screw assembly used in a bone fixation system with an anti-back out feature taken along line C-C.

FIG. 6A is a cross-section of one embodiment of an orthopedic plate, clamp, and screw assembly used in a bone fixation system with an anti-back out feature taken along line C-C of FIG. 1. The head of screws 10 sits within the space defined by the hole 42 in the plate 40, and, as the head is driven toward the bone, the plate is compressed against the bone. The screw 10 can be driven until a desired compression is obtained. The conical taper 16 of the screws 10 sits against the conical taper of the screw holes 42. The conical configuration of both the screw head and the screw hole allow the screws 10 to be inserted either perpendicularly or at an angle into the bone and to provide the desired compression.

The clamp 30, and more specifically the protrusions 34, prevents any loosening or back out of the screw 10 that may occur through micromotion. Due to the conical taper 16 at the lower end of the head of the screw 10, the screw 10 can be inserted into the screw hole 42 and past the clamp 30 without significant resistance from the clamp 30, as the conical taper 16 presents a ramped surface that will partially deflect the clamp 30 into the notch and channel 46 of the hole 42 as the screw is inserted. However, the configuration of the screw 10 with the cylindrical portion 22 that has a radius smaller than that of the rest of the screw head allows the protrusions 34 of the clamp 30 to rest on surface 14 of the screw. With this arrangement, significant interference can be created between the protrusions 34 and the head of the screw 10. As such, the clamp 30 resists unintentional backing out by the screw 10 from the screw hole and can be configured, for example, so that such resistance can be overcome with substantial and intentional manual force applied to the screw.

Figure 6B:
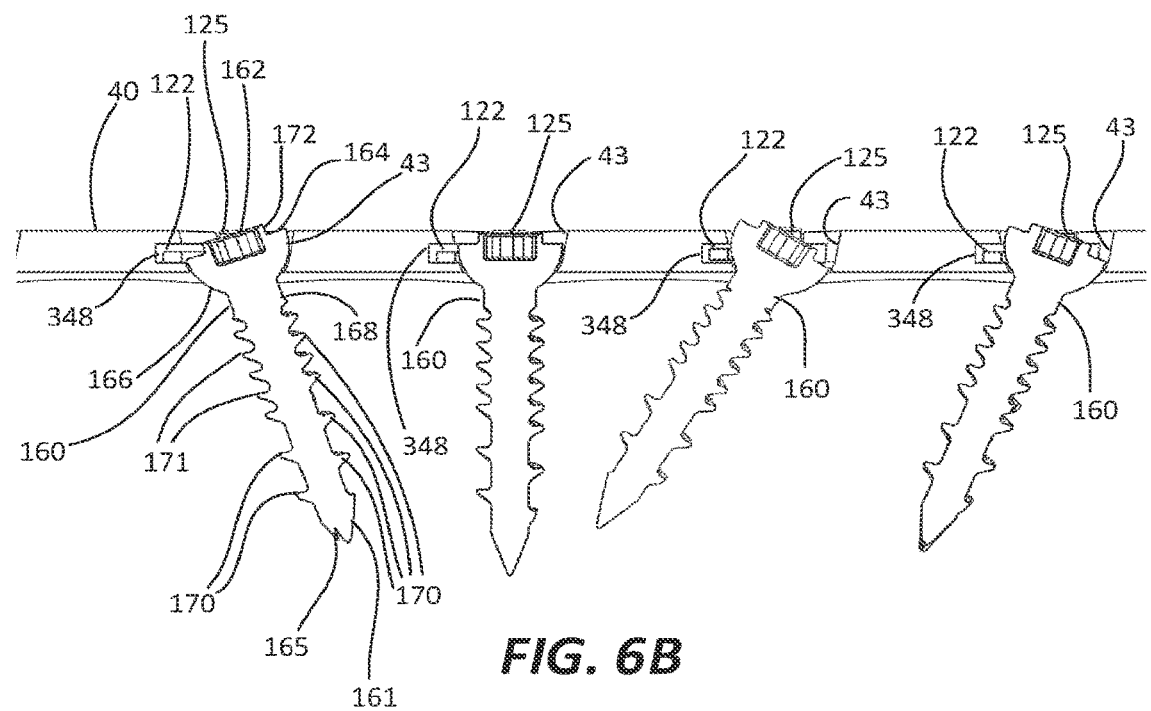
FIG. 6B is a cross-section of one embodiment of an orthopedic plate, clamp, and screw assembly used in a bone fixation system with an anti-back out feature.

FIG. 6B is a cross-section of one embodiment of an orthopedic plate, clamp, and screw assembly used in a bone fixation system with an anti-back out feature. The embodiment shown in FIG. 6B includes an orthopedic plate such as orthopedic plate 40 of FIG. 1, a locking clip such as single hole locking clip 203 of FIG. 30, and a screw such as fully threaded axially displaced double-lead threaded screw 160 of FIG. 25. Other embodiments may comprise other orthopedic plates, other locking clip, and other screws, as described elsewhere herein.

Orthopedic plate 40 can have multiple instances of frustoconical internal surface 43, each instance of which defines a hole 42 in orthopedic plate 40. Defined within internal surface 43 is arcuate undercut cavity 348. Arcuate undercut cavity 348 serves as a housing for connective portion 122 of single hole locking clip 203 to retain single hole locking clip 203 securely within orthopedic plate 40.

Screw 160 comprises single lead wide pitch thread 170 forms a helix that extends along a threaded length of screw 160. Additional wide pitch thread 171 forms a helix whose turns lie between the turns of single lead wide pitch thread 170 along the same axis as single lead wide pitch thread 170. Thus, alternations of single lead wide pitch thread 170 and additional wide pitch thread 171 lie along a proximal portion of screw 160 above the distal portion of screw 160 where additional wide pitch thread 171 is not present.

Screw 160 comprises a self-drilling tip 161. The self-drilling tip can have a cutting edge (shown in FIG. 25) and a following edge 165 that define an angular cavity in self-drilling tip 161 that can serve as a straight flute to expose the cutting edge.

Screw 160 comprises a cylindrical portion 168 between the proximal terminations of single lead wide pitch thread 170 and additional wide pitch thread 171 and a circular distal edge of convexly curved distal portion 166 of the head of screw 160. An annular ledge 164 is defined at the proximal edge of convexly curved distal portion 166 of the head of screw 160. In the illustrated embodiment, a cylindrical riser 172 lies proximal to (e.g., above) annular ledge 164, and cylindrical riser 172 rises to an upper end surface 162. Upper end surface 162 may be planar. A cavity may be defined in upper end surface 162 to accept a screwdriver for driving screw 160 into and out of a material, such as bone. The cavity defined in upper end surface 162 may, for example, be multi-lobular, polygonal, or multi-slotted.

Single hole locking clip 203 comprises a locking tab 125. Locking tab 125 has an underside surface to engage annular ledge 164 of screw 160 after screw 160 has been driven far enough to allow locking tab 125 to clear convexly curved distal portion 166 of screw 160. When annular ledge 164 is engaged by locking tab 125, screw 160 is prevented from backing out of hole 42.

Figure 7:
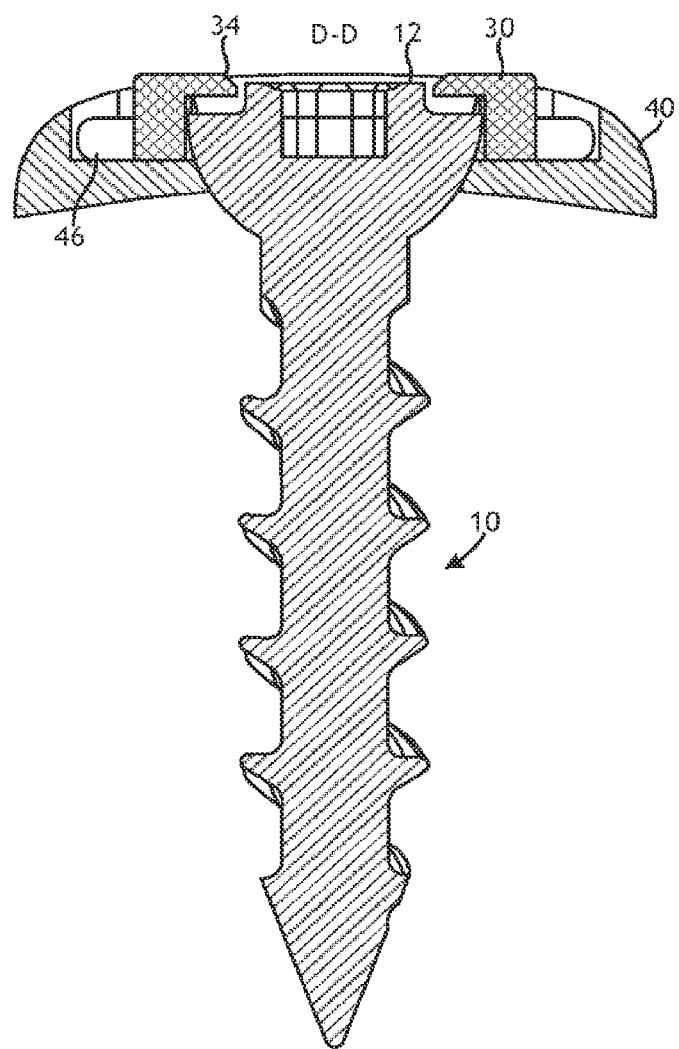
FIG. 7 is a cross-section of one embodiment of an orthopedic plate, clamp, and screw assembly used in a bone fixation system with an anti-back out feature taken along line D-D.

FIG. 7 is a cross-section of one embodiment of an orthopedic plate, clamp, and screw assembly used in a bone fixation system taken along line D-D of FIG. 1, showing the interference between the protrusions 34 of the clamp 30 and the screw 10. As discussed above, the clamp 30 sits within the notch and channel 46 of the screw hole 42. The protrusions 34 of the clamp prevent the back out of the screw 10. In addition, if screw removal is necessary, the clamp 30 may be positioned within the notch and channel 46 to position the clamp 30 to facilitate screw removal. Moreover, the protrusions 34 of the clamp need not cover surface 12 of the orthopedic screw 10, thus they need not impede access for an instrument to be positioned to remove the screw 10.

Figure 8:
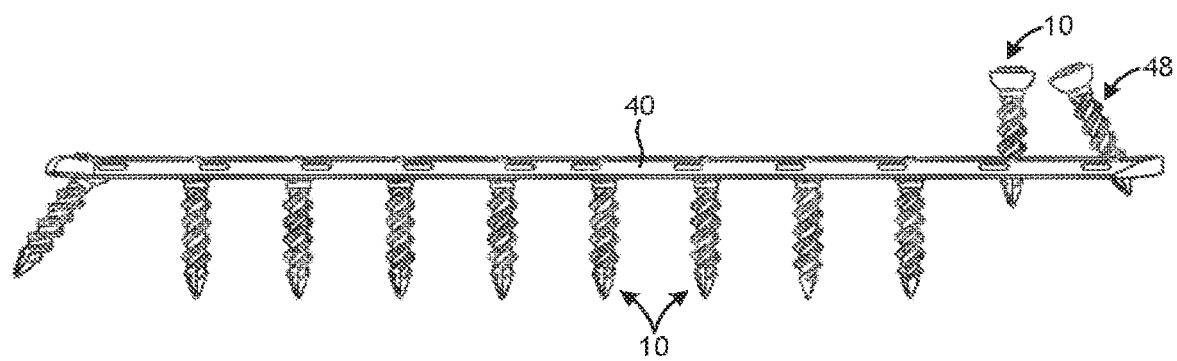
FIG. 8 is a side view of one embodiment of an orthopedic plate, clamp, and screw assembly used in a bone fixation system.

FIG. 8 is a side view of one embodiment of an orthopedic plate, clamp, and screw assembly used in a bone fixation system. Orthopedic screws 10, 48 can be inserted into the bone (not shown) through screw holes 42 in the orthopedic plate 40. As discussed above, the conical configuration of the screw head and screw holes allow the screws 10, 48 to be inserted into the bone either perpendicularly (see screws 10) or at an angle (see screw 48), while still providing the desired compression.

Figure 9:
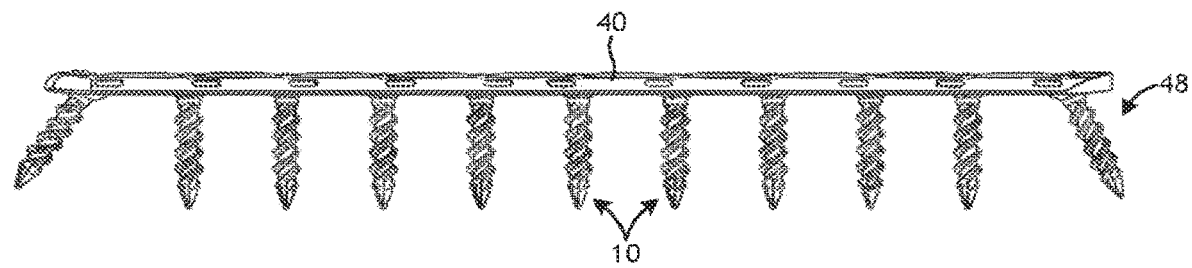
FIG. 9 is another side view of one embodiment of an orthopedic plate, clamp, and screw assembly used in a bone fixation system.

FIG. 9 is another side view of one embodiment of an orthopedic plate, clamp, and screw assembly used in a bone fixation system. In such an embodiment, the orthopedic plate 40 may be attached to the bone(s) by placing the plate 40 on the bone and securing the plate 40 to the bone with a plurality of orthopedic screws 10 through a plurality of holes 42 in the plate 40. In another embodiment, the plate 40 may be secured to the bone with an orthopedic screw 48 in a first hole in the plate located at one longitudinal end of the plate. After the first screw 48 is properly inserted, a traction (or horizontal) force may be applied to the opposite end of the plate 40. While still applying the traction force to the plate 40, the plate 40 may be further secured to the bone with at least one orthopedic screw 10, here an additional ten screws 10, placed in one or more of the remaining holes 42 of the plate.

Figure 10:
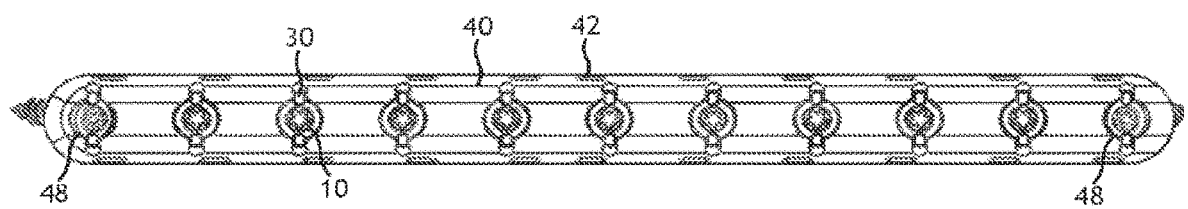
FIG. 10 is a top view of one embodiment of an orthopedic plate, clamp, and screw assembly used in a bone fixation system.

FIG. 10 is a top view of one embodiment of an orthopedic plate, clamp, and screw assembly used in a bone fixation system. As described above, a plurality of screws 10, 48 can be inserted into the bone (not shown) through screw holes in the orthopedic plate 40. Optional openings 42 in the plate 40 can provide visual access to the underlying bone. The protrusions 34 of clamps 30 cover a portion of the head of screws 10, 48 to prevent back out.

Figure 11:
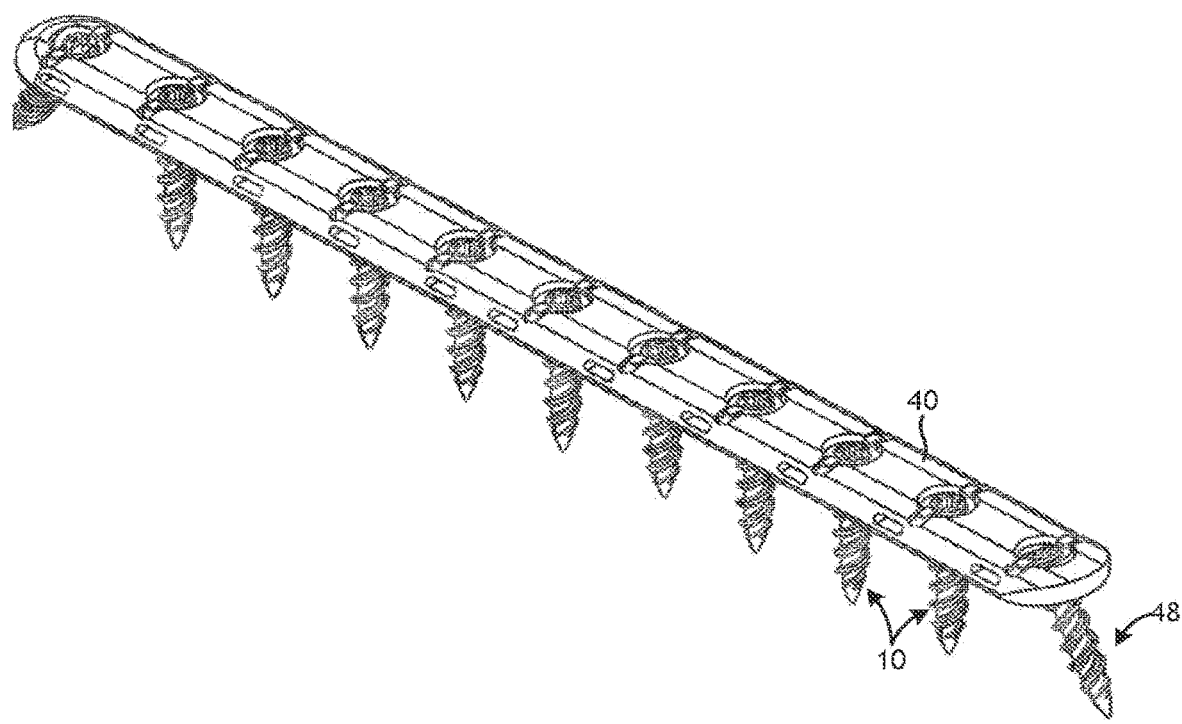
FIG. 11 is a perspective view of one embodiment of an orthopedic plate, clamp, and screw assembly used in a bone fixation system.

FIG. 11 is a perspective view of one embodiment of an orthopedic plate, clamp, and screw assembly used in a bone fixation system. As discussed, a surface of the orthopedic plate 40 may be curved to complement the natural curved structure of a bone. The orthopedic screws 10 can be inserted perpendicularly into the bone. The orthopedic screws 48 can be inserted into the bone at an angle. An element such as the clamp described above can serve as a locking clip to lock a fastener in place. Thus, the term "locking clip," as used herein can include embodiments of the "clamp" described above. By locking a fastener in place, a locking clip may provide a clearance to tolerate some amount of micromotion between the fastener and the bone, during which the fastener may back out very slightly, but gross backing out of the fastener can be prevented.

Figure 12:
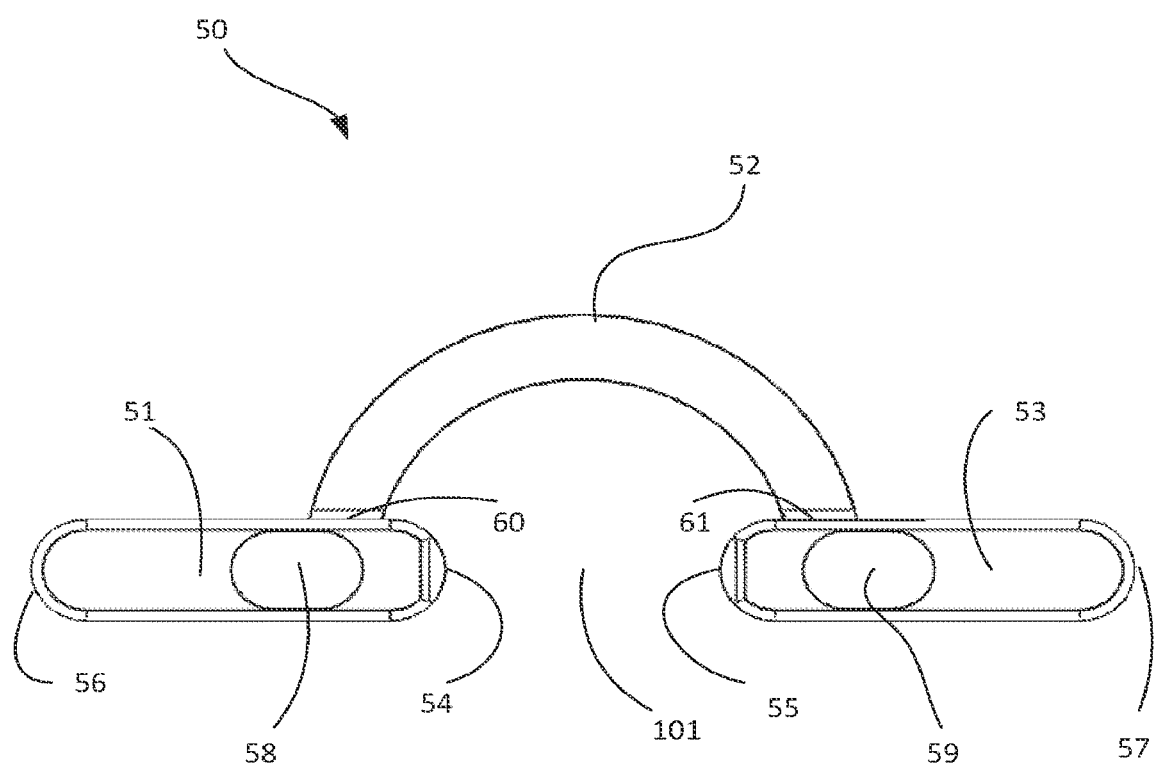
FIG. 12 is a plan view diagram illustrating a straight three hole locking clip in accordance with at least one embodiment.

FIG. 12 is a plan view diagram illustrating a straight three hole locking clip in accordance with at least one embodiment. Straight three hole locking clip 50 comprises a first substantially straight portion 51, a connective portion 52, and a second substantially straight portion 53. First substantially straight portion 51 is connected to connective portion 52 at junction 60. Second substantially straight portion 53 is connected to connective portion 52 at junction 61. Connective portion 52 serves to maintain a structural relationship between first substantially straight portion 51 and second substantially straight portion 53. Connective portion 52 is configured so as not to obstruct a path of a screw by defining a space 101 through which the screw may pass and where the screw head may be situated and retained by straight three hole locking clip 50. In the illustrated embodiment, connective portion 52 is of an arcuate shape defining a semicircular opening through which a screw may pass. As an example, connective portion 52 may define an inner radius of curvature of at least the radius of a head of a screw to be retained by the central portion of the straight three hole locking clip.

At a medial end of first substantially straight portion 51 is defined a locking tab 54. At a medial end of second substantially straight portion 53 is defined a locking tab 55. Locking tab 54 and locking tab 55 are configured to oppose one another, for example, to diametrically oppose one another with respect to a diameter of a screw to be retained by locking tabs 54 and 55.

At a lateral end of first substantially straight portion 51 is defined a locking tab 56. Locking tab 56 is configured to retain a screw to be installed lateral to most of first substantially straight portion 51 but with locking tab 56 overhanging a portion of the head of the screw. At a lateral end of second substantially straight portion 53 is defined a locking tab 57. Locking tab 57 is configured to retain a screw to be installed lateral to most of second substantially straight portion 53 but with locking tab 57 overhanging a portion of the head of the screw. Thus, three screws can be retained using straight three hole locking clip 50, with one screw retained by locking tabs 54 and 55, another screw retained by locking tab 56, and another screw retained by locking tab 57.

A first clip tool engagement cavity 58 is defined in first substantially straight portion 51. A second clip tool engagement cavity 59 is defined in second substantially straight portion 53. A clip tool, such as a spring clip tool having two prongs, wherein the distance between the prongs can be adjusted, for example, using handles of the tool, can be used to compress or expand straight three hole locking clip 50. One prong of the clip tool can be placed in first clip tool engagement cavity 58, the other prong of the clip tool can be placed in second clip tool engagement cavity 59, and the distance between the prongs can be adjusted to bring first substantially straight portion 51 closer to, or farther from, second substantially straight portion 53. Depending on the flexibility of connective portion 52, the angle between first substantially straight portion 51 and second substantially straight portion can be changed, for example, to be greater or less than an angle in a neutral position of straight three hole locking clip 50, which may, for example, be 180 degrees. Even if connective portion 52 is stiff enough to make any flexure negligible, pressure exerted by prongs of a clip tool in first clip tool engagement cavity 58 and second clip tool engagement cavity 59 can provide a rigid grip of the clip tool on straight three hole locking clip 50. The clip tool may be used to maneuver straight three hole locking clip 50 into or out of a recess in a plate, for example, to install or to remove straight three hole locking clip 50 into or out of the plate.

As the prongs of the clip tool may or may not be parallel to one another, first clip tool engagement cavity 58 and second clip tool engagement cavity 59 may be cylindrical or may be elongated to define a slot with semicylindrical ends. As an example, a clip tool having one prong fixedly situated with respect to one handle and another prong fixedly situated with respect to another handle, with the two pieces joined at a pivot point, may have the prongs extending radially with respect to the pivot point such that the prongs are not parallel to one another. An elongated form of first clip tool engagement cavity 58 and second clip tool engagement cavity 59 can accommodate the divergence of non-parallel clip tool prongs.

Figure 13:
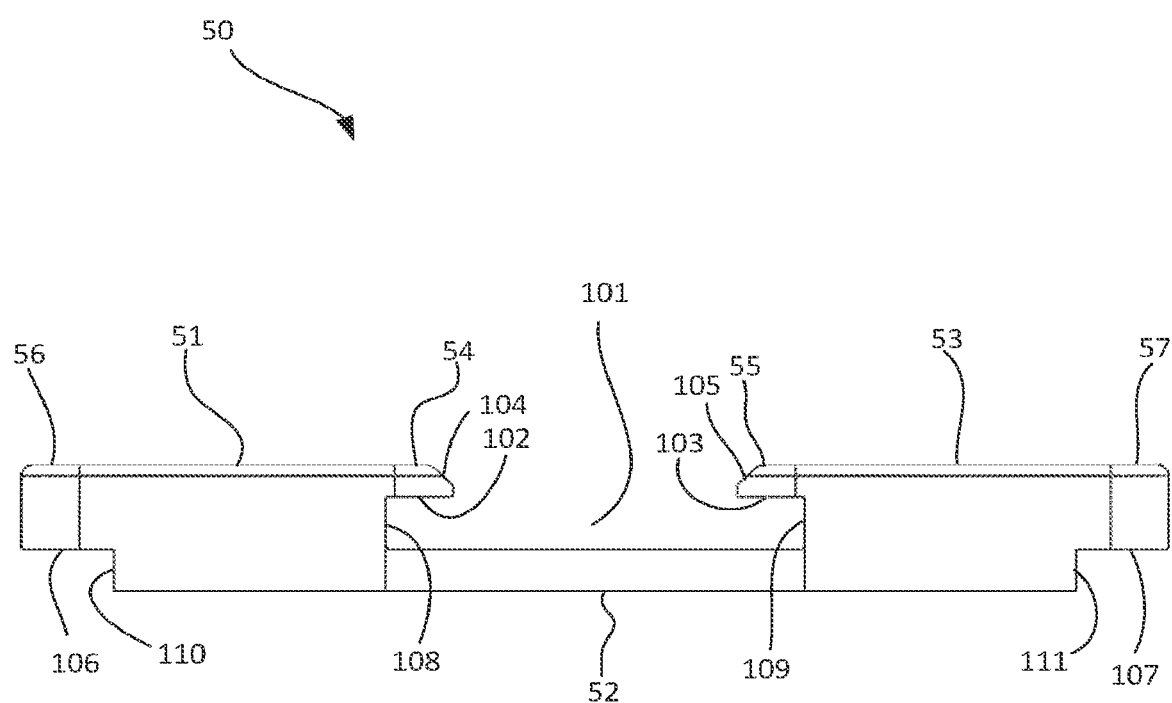
FIG. 13 is a front elevation view diagram illustrating a straight three hole locking clip in accordance with at least one embodiment.

FIG. 13 is a front elevation view diagram illustrating a straight three hole locking clip in accordance with at least one embodiment. The opposing relationship of locking tabs 54 and 55 can be seen, as can the manner in which locking tabs 54 and 55 overhang space 101 in which a screw head may be installed. While the flexibility of connective portion 52 allows a screw head to displace locking tabs 54 and 55 enough to allow the screw head to pass locking tabs 54 and 55, the spring tension of connective portion 52 in the displaced state biases locking tabs 54 and 55 to return to their neutral positions once the screw head has passed below the underside surfaces 102 and 103 of locking tabs 54 and 55, respectively, to assume the installed position of the screw head between wall 108 of first substantially straight portion 51 and wall 109 of second substantially straight portion 53. Locking tabs 54 and 55 may be chamfered, as illustrated by chamfer 104 of locking tab 54 and chamfer 105 of locking tab 55, to translate the downward force of the screw head against locking tabs 54 and 55 into a lateral spreading force to displace locking tabs 54 and 55 in opposite directions to allow the screw head to pass locking tabs 54 and 55.

Locking tabs 56 and 57 define underside surfaces 106 and 107, respectively, which are elevated by walls 110 and 111, respectively. By providing a cavity in the plate in which straight three hole locking clip 50 may be installed that allows straight three hole locking clip 50 some freedom to move laterally, three screws can be installed sequentially with the end result that all three screws are retained by three hole locking clip 50. For example, by translating straight three hole locking clip 50 rightward relative to the view of FIG. 13, locking tab 56 can be moved out of the path of a first screw to be installed left of locking tab 56. After installing such first screw, straight three hole locking clip 50 can be moved leftward relative to the view of FIG. 13, moving locking tab 56 over the installed screw head and moving locking tab 57 out of the path of a second screw to be installed to the right of locking tab 57. Then, straight three hole locking clip 50 can be moved back to a centered position, leaving a portion of locking tab 56 extending over the first screw head to retain the first screw head and a portion of locking tab 57 extending over the second screw head to retain the second screw head. Then, a third screw can be installed through space 101, displacing locking tabs 54 and 55 in opposite directions until the third screw head passes below underside surface 102 and 103, at which point locking tabs 54 and 55 return to their neutral positions, retaining the third screw head. With the third screw head installed, the sides of the third screw head blocks movement of straight three hole locking clip 50 to the left or right due to the presence of walls 108 and 109, respectively, adjacent to the third screw head. Accordingly, the installed third screw head keeps straight three hole locking clip 50 centered such that locking tab 56 maintains retention of the first screw head and locking tab 57 maintains retention of the second screw head.

Figure 14:
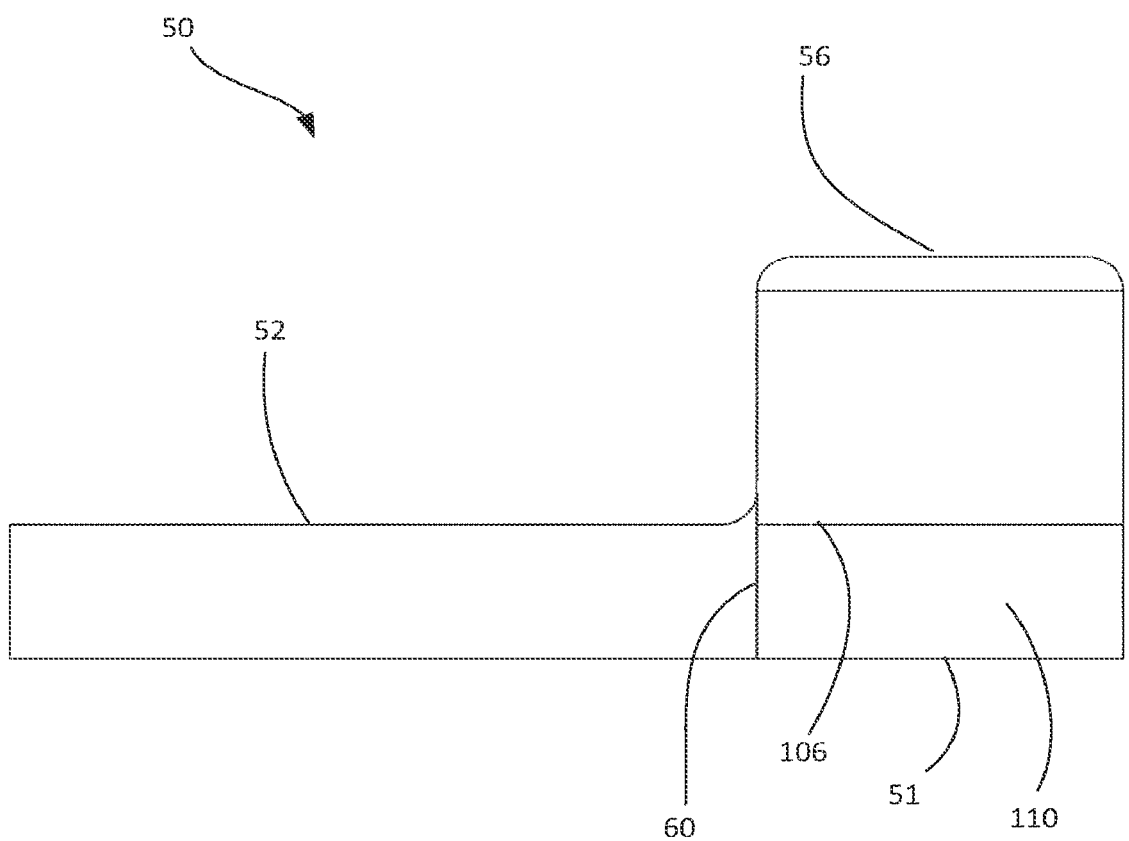
FIG. 14 is a side elevation view diagram illustrating a straight three hole locking clip in accordance with at least one embodiment.

FIG. 14 is a side elevation view diagram illustrating a straight three hole locking clip 50 in accordance with at least one embodiment. As viewed from the end of first substantially straight portion 51 at which locking tab 56 is located, the edge of underside surface 106 of locking tab 56 and wall 110 are illustrated. A proximal end of connective portion 52 is connected to first substantially straight portion 51 at junction 60.

Figure 15:
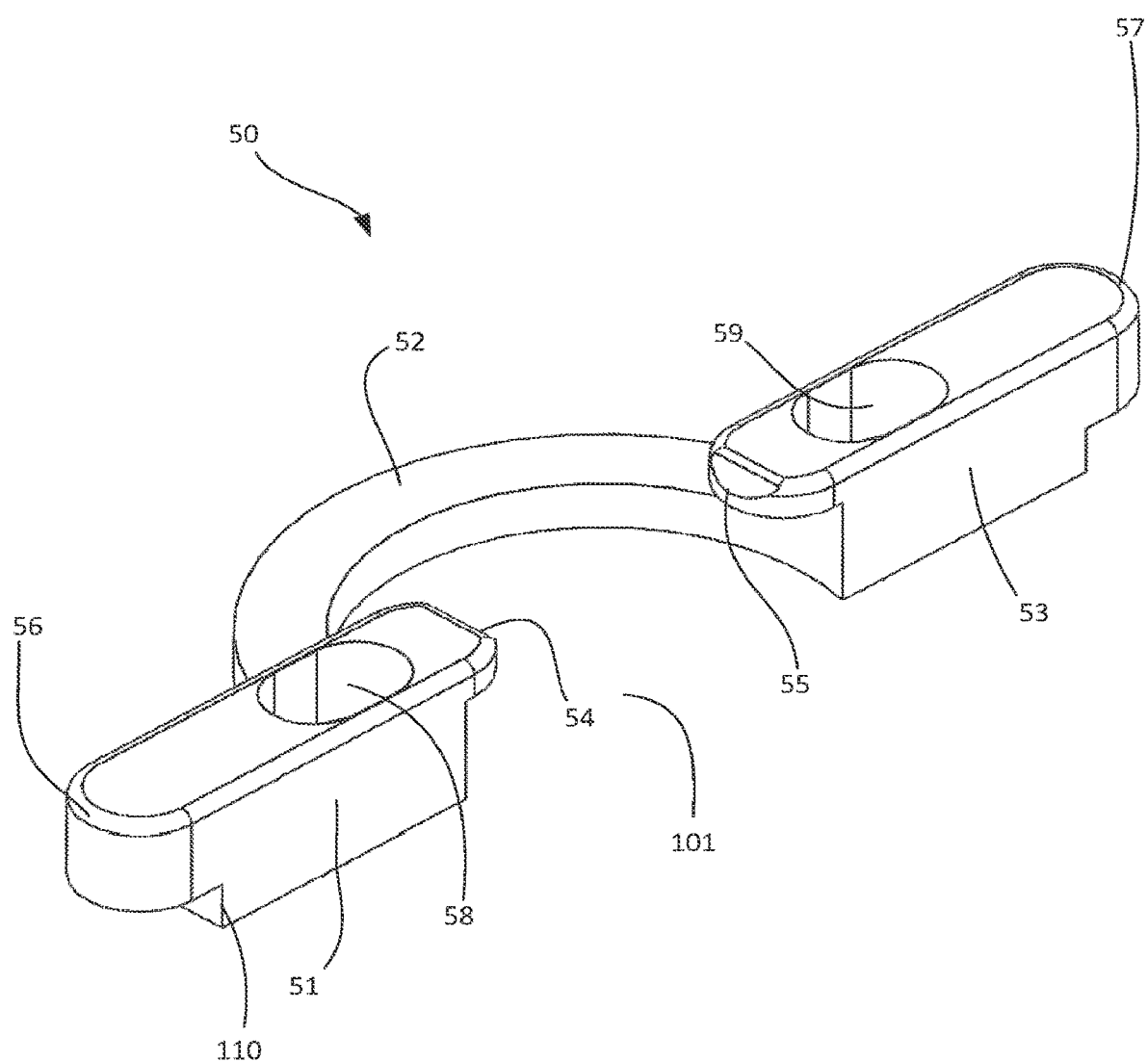
FIG. 15 is a perspective view diagram illustrating a straight three hole locking clip in accordance with at least one embodiment.

FIG. 15 is a perspective view diagram illustrating a straight three hole locking clip in accordance with at least one embodiment. The elements shown in FIG. 15 are as described in reference to FIGS. 12 through 14 above.

In accordance with at least one embodiment, a locking clip is provided for retaining a fastener in a bone fixation plate. The locking clip comprises a flexure member and a body member coupled to the flexure member. The example illustrated in FIG. 15 includes a flexure member comprising retention portion 52. That example further includes a first body member comprising first substantially straight portion 51 and a second body member comprising second substantially straight portion 53. A body member comprises a locking tab. In the example of FIG. 15, the first body member comprises first locking tab 56 and second locking tab 54, and the second body member comprises third locking tab 57 and fourth locking tab 55. A locking tab is configured to provide an axial limitation to motion of the fastener in a non-rotationally-ratcheting manner. The flexure member resiliently flexible to permit displacement of the locking tab to allow passage of a fastener head of the fastener. Other examples of flexure members and body members can be seen in other FIGs. described herein illustrating examples of a locking clip.

Figure 16:
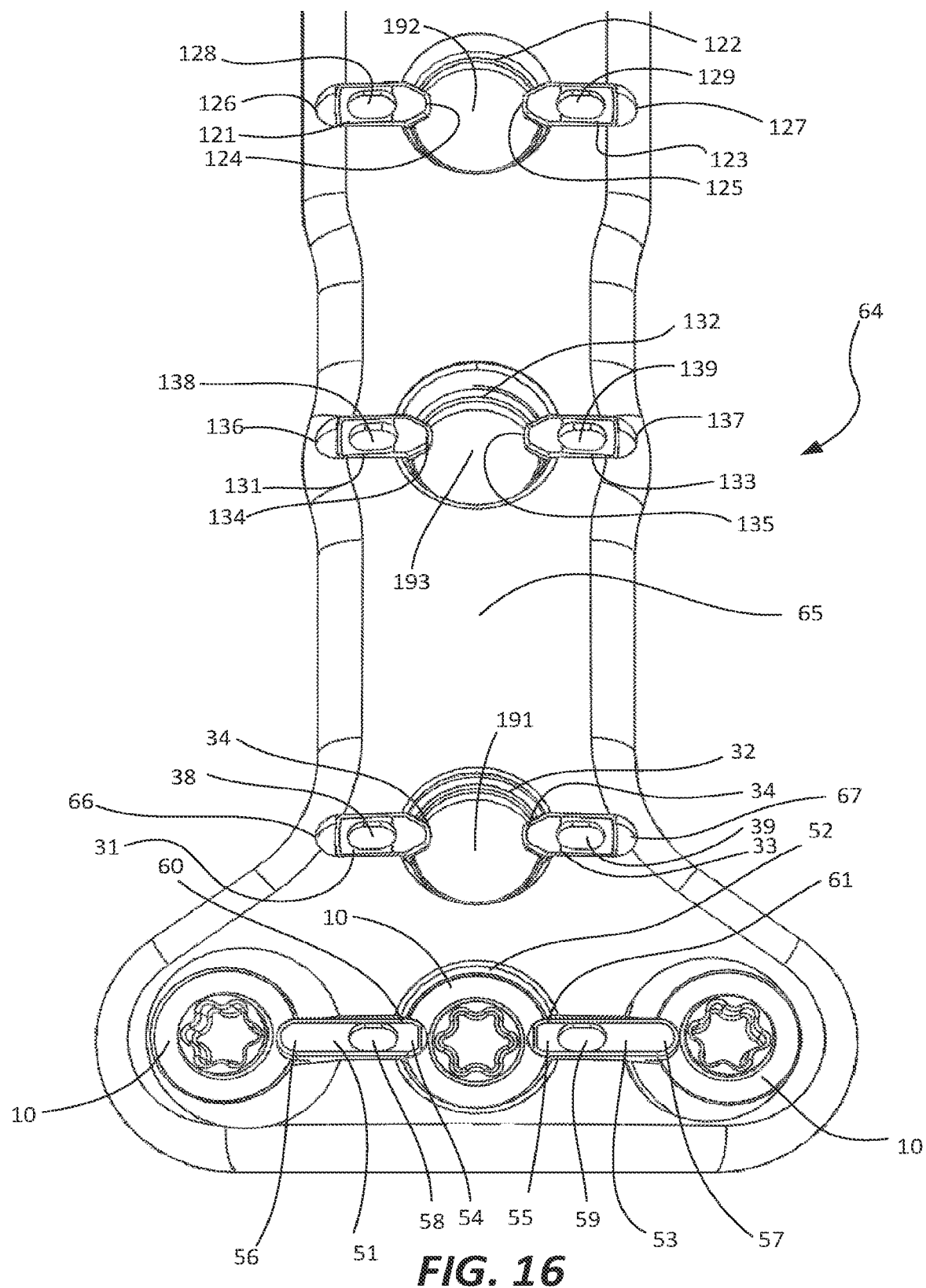
FIG. 16 is a plan view diagram illustrating a plate assembly incorporating a straight three hole locking clip in accordance with at least one embodiment.

FIG. 16 is a plan view diagram illustrating a plate assembly incorporating a straight three hole locking clip in accordance with at least one embodiment. Plate assembly 64 comprises plate 65 and several installed locking clips. Straight three hole locking clip 50 may be installed in plate 65 at a widened end of plate 65. Straight three hole locking clip 50 is shown retaining three screws 10. Straight hole locking clip 50 comprises a locking tab 56 retaining a screw 10 on the left, locking tabs 54 and 55 retaining a screw 10 in the center, and locking tab 57 retaining a screw 10 on the right. Locking tab 56 is located at an outer end of first substantially straight portion 51 of straight three hole locking clip 50. Locking tab 54 is located at an inner end of first substantially straight portion 51. Locking tab 55 is located at an inner end of second substantially straight portion 53 of straight three hole locking clip 50. Locking tab 57 is located at an outer end of second substantially straight portion 53. Connective portion 52 connects first substantially straight portion 51 to second substantially straight portion 53, meeting first substantially straight portion 51 at junction 60 and meeting second substantially straight portion 53 at junction 61. First clip tool engagement cavity 58 is defined in first substantially straight portion 51. Second clip tool engagement cavity 59 is defined in second substantially straight portion 53.

Three single hole locking clips are also installed in plate 65. A first single hole locking clip comprises a first substantially straight portion 31, a washer 32, and second substantially straight portion 33, with washer 32 connecting first substantially straight portion 31 to second substantially straight portion 33 in a manner that affords a space 191 through which a fastener component, such as an orthopedic screw, can pass. The space 191 provided by washer 32 can be large enough not to obstruct the head of the fastener, while a hole defined in plate 65 can be of a smaller diameter to prevent the entire head of the fastener from passing through plate 65, allowing the head of the fastener to exert force against plate 65 to affix plate 65 to bone underlying plate 65 into which the screw may be threaded.

First substantially straight portion 31 comprises a protrusion 34 that protrudes inwardly above the space 191 afforded by washer 32. Second substantially straight portion 33 comprises a protrusion 34 that protrudes inwardly above the space afforded by washer 32. Protrusions 34 can retain a fastener head, such as a screw head, in space 191.

First substantially straight portion 31 comprises first clip tool engagement cavity 38. Second substantially straight portion 33 comprises second clip tool engagement cavity 39. Tips of a clip tool can be inserted in first clip tool engagement cavity 38 and second clip tool engagement cavity 39.

By spreading the tips of the clip tool, first substantially straight portion 31 and second substantially straight portion 33 can be spread apart from one another, allowing protrusions 34 to be spread apart from one another enough that the fastener head can pass between protrusions 34, allowing the fastener to be removed from space 191. A cavity 66 is defined in plate 65 at the outer end of first substantially straight portion 31. A cavity 67 is defined in plate 65 at the outer end of second substantially straight portion 33. Cavity 66 allows for lateral displacement of first substantially straight portion 31 either to allow spreading of protrusions 34 as a fastener is installed or to allow spreading of protrusions 34 through the use of a clip tool whose tips can be engaged in first clip tool engagement cavity 38 and second clip tool engagement cavity 39 for removal of the fastener.

A second single hole locking clip comprises first substantially straight portion 121, second substantially straight portion 123, and connective portion 122. Connective portion 122 connects first substantially straight portion 121 to second substantially straight portion 123. Connective portion 122 has a shape, such as an arcuate shape, that defines a space 192 in which a fastener head, such as a screw head, may be situated. First substantially straight portion 121 comprises a locking tab 124 at its inner end. Second substantially straight portion 123 comprises a locking tab 125 at its inner end, facing locking tab 124. A fastener, such as a screw, whose head may be situated in space 192 would be retained by locking tabs 124 and 125, preventing the fastener from backing out.

First clip tool engagement cavity 128 is defined in a top surface of first substantially straight portion 121. Second clip tool engagement cavity 129 is defined in a top surface of second substantially straight portion 123. A clip tool whose tips can be inserted into first clip tool engagement cavity 128 and second clip tool engagement cavity 129 can be used to spread first substantially straight portion 121 and second substantially straight portion 123 apart, causing locking tab 124 to be spread apart from locking tab 125, which can allow a fastener head to pass between locking tabs 124 and 125, allowing the fastener to be removed after installation. Cavity 126 is defined in plate 65 beyond an outer end of first substantially straight portion 121. Cavity 127 is defined in plate 65 beyond an outer end of second substantially straight portion 123. Cavity 126 provides clearance to allow first substantially straight portion 121 to be displaced outwardly, either by a wedging action of a fastener head during fastener installation or by a spreading action through the use of a clip tool during fastener removal, which can allow the fastener head to pass between locking tab 124 and locking tab 125. Cavity 127 provides clearance to allow second substantially straight portion 123 to be displaced outwardly in similar circumstances, allowing the fastener head to pass between locking tab 124 and locking tab 125.

A third single hole locking clip comprises first substantially straight portion 131, connective portion 132, and second substantially straight portion 133. First substantially straight portion 131 comprises locking tab 134. Second substantially straight portion 133 comprises locking tab 135. First clip tool engagement cavity 138 is defined in a top surface of first substantially straight portion 131. Second clip tool engagement cavity 139 is defined in a top surface of second substantially straight portion 133. Cavity 136 is defined in plate 65 beyond an outer end of first substantially straight portion 131. Cavity 137 is defined in plate 65 beyond an outer end of second substantially straight portion 133.

Figure 17:
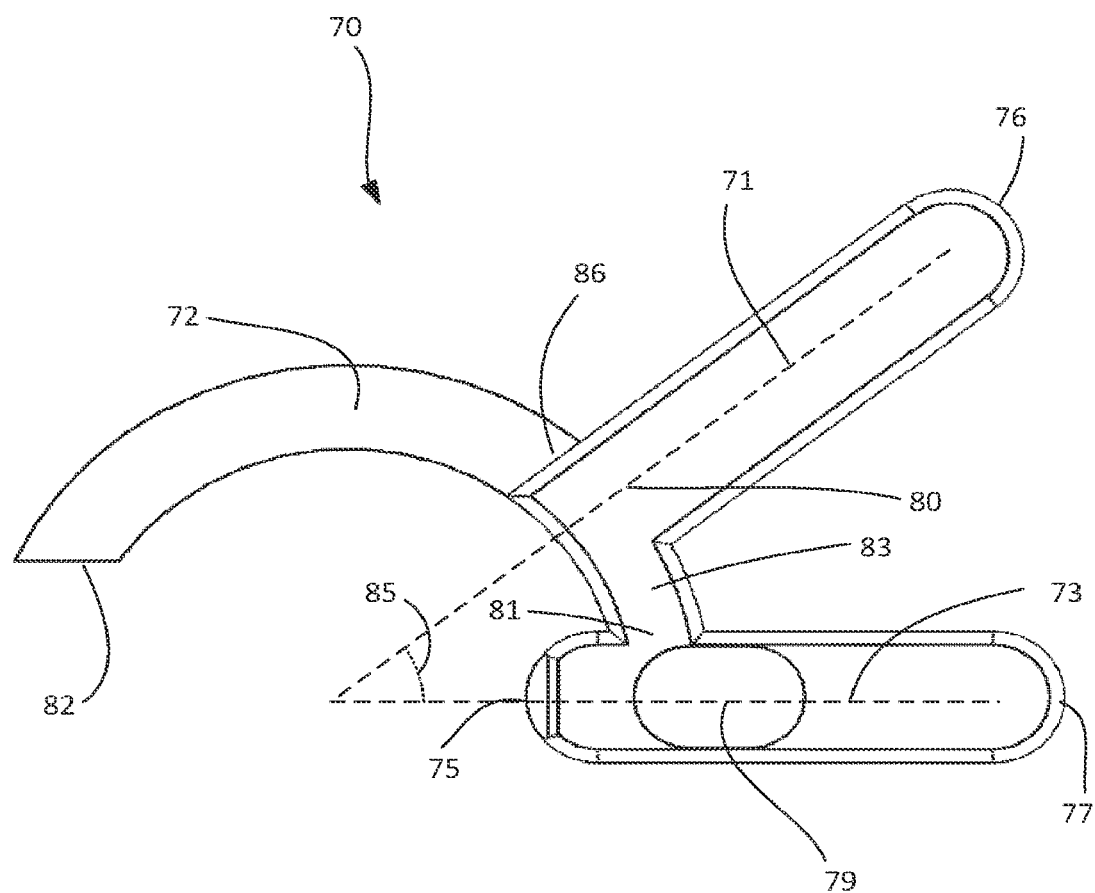
FIG. 17 is a plan view diagram illustrating an angled three hole locking clip in accordance with at least one embodiment.

FIG. 17 is a plan view diagram illustrating an angled three hole locking clip in accordance with at least one embodiment. Angled three hole locking clip 70 comprises retention portion 72, first substantially straight portion 71, connective portion 83, and second substantially straight portion 73. Retention portion 72 extends from an end 82 to a junction 86 with an inner end of first substantially straight portion 71. Connective portion 83 extends from an edge of the inner end of first substantially straight portion 71 opposite junction 86 to junction 81 with second substantially straight portion 73.

First substantially straight portion 71 comprises a locking tab 76 at its outer end. Second substantially straight portion 73 comprises a locking tab 77 at its outer end. Second substantially straight portion 73 comprises a locking tab 75 at its inner end. While retention portion 72 and connective portion 83 may follow similar arcuate contours, first substantially straight portion 71 extends radially outward beyond junction 80 with the outer arcuate contour along which retention portion 72 and connective portion 83 lie. Clip tool engagement cavity 79 is defined in an upper surface of second substantially straight portion 73. Clip tool engagement cavity 79 allows a tip of a clip tool to be inserted in clip tool engagement cavity 79 to bias second substantially straight portion 73 to be translated inwardly or outwardly to provide clearance of a screw head past locking tab 77 or locking tab 75, respectively, so that one or more screws may be removed from the orthopedic plate in which angled three hole locking clip 70 can be installed.

First substantially straight portion 71 lies along a first radial axis. Second substantially straight portion 73 lies along a second radial axis. An angle 85 between the first radial axis and the second radial axis. Unlike the straight three hole locking clip where the corresponding angle is 180 degrees, angled three hold locking clip 70 has an angle 85 of less than 180 degrees. As an example, angle 85 may be in the range of 10 degrees to 90 degrees. As another example, angle 85 may be in the range of 15 degrees to 80 degrees. As another example, angle 85 may be in the range of 20 degrees to 70 degrees. As another example, angle 85 may be in the range of 25 degrees to 60 degrees. As another example, angle 85 may be in the range of 30 to 50 degrees.

Figure 18:
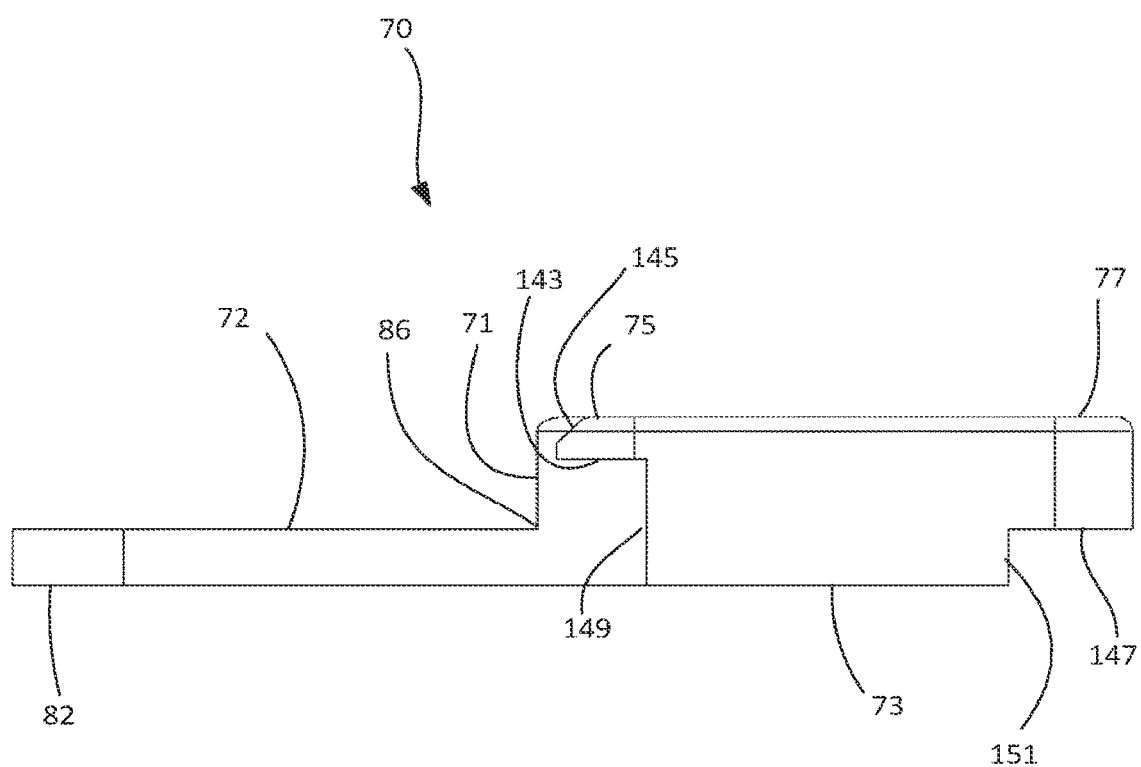
FIG. 18 is a front elevation view diagram illustrating an angled three hole locking clip in accordance with at least one embodiment.

FIG. 18 is a front elevation view diagram illustrating an angled three hole locking clip in accordance with at least one embodiment. Angled three hole locking clip 70 comprises retention portion 72 extending from end 82 to junction 86 with first substantially straight portion 71.

Second substantially straight portion 73 defines a locking tab 75 at its inner end and a locking tab 77 at its outer end. Locking tab 75 comprises a chamfer 145 between its end and its upper surface. Chamfer 145 can act as a wedge to interact with a fastener head to force second substantially straight portion 73 to move outwardly to allow the fastener to be installed. Locking tab 75 has an underside surface 143. When locking tab 75 is returned to its normal position, for example, by force exerted on retention portion 72 by an installed fastener head, underside surface 143 can serve to retain the fastener head and prevent the fastener from backing out. Underside surface 143 of locking tab 75 intersects vertical wall 149 of second substantially straight portion 73. Locking tab 77 has an underside surface 147. Underside surface 147 can retain a fastener at the outer end of second substantially straight portion 73. Underside surface 147 intersects vertical wall 151 of second substantially straight portion 73.

Figure 19:
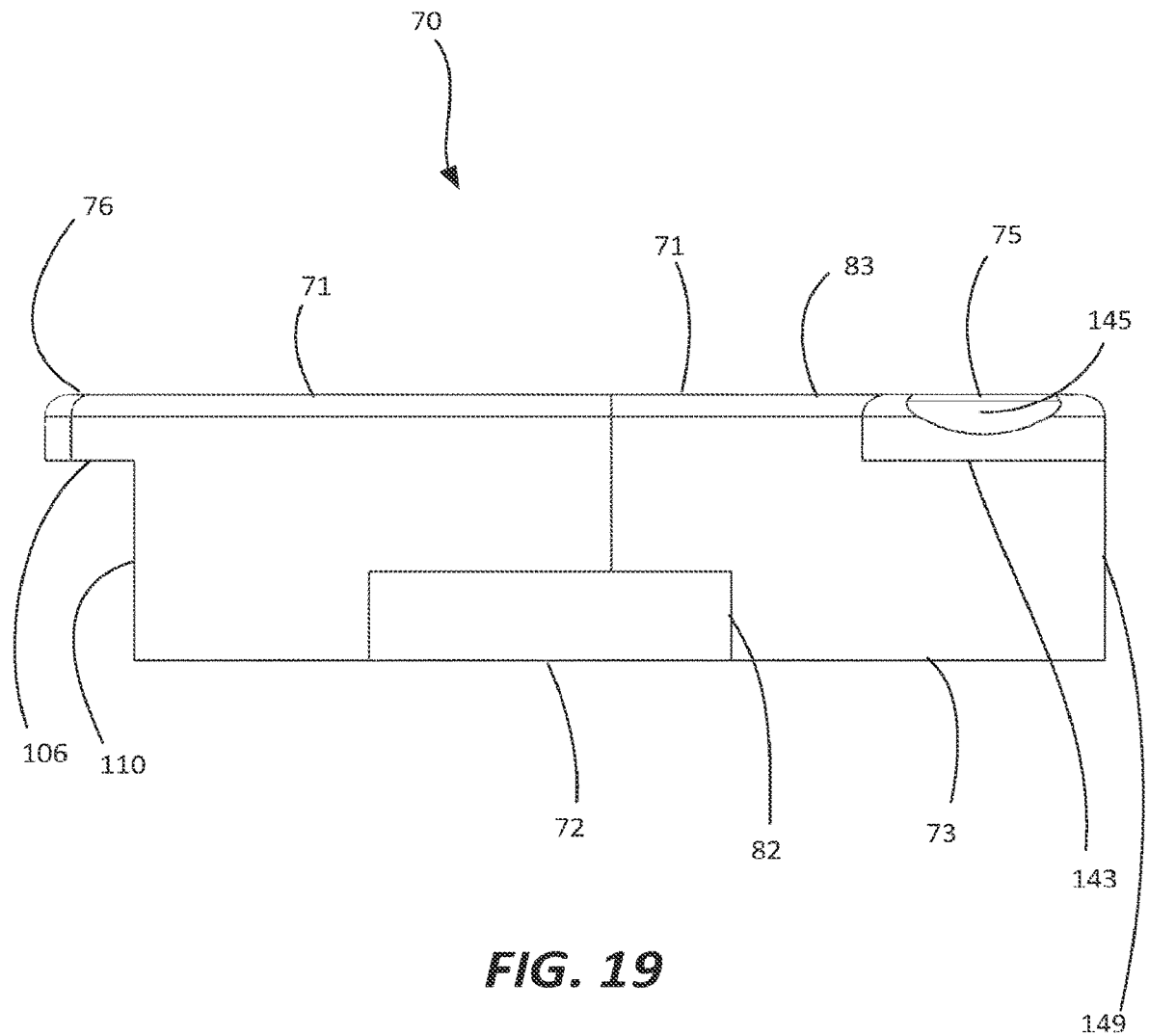
FIG. 19 is a side elevation view diagram illustrating an angled three hole locking clip in accordance with at least one embodiment.

FIG. 19 is a side elevation view diagram illustrating an angled three hole locking clip in accordance with at least one embodiment. Angled three hole locking clip 70 comprises retention portion 72, ending at end 82. Angled three hole locking clip 70 comprises first substantially straight portion 71, which extends radially to locking tab 76 at its outermost extent. Locking tab 76 has an underside surface 106, which can bear against a portion of a top of a fastener head to retain the fastener head and prevent the fastener from backing out. Underside surface 106 intersects vertical wall 110 of first substantially straight portion 71.

First substantially straight portion 71 is joined to second substantially straight portion 73 by connective portion 83. Second substantially straight portion 73 extends inwardly to locking tab 75. Locking tab 75 may comprises chamfer 145. Chamfer 145 can bear against a surface of a fastener head to serve as a wedge to force locking tab 75 away from the path of the fastener head to allow installation of the fastener. Locking tab 75 has an underside surface 143, which can bear against a portion of a top of a fastener head to retain the fastener head and prevent the fastener from backing out. Underside surface 143 intersects vertical wall 149 of second substantially straight portion 73.

Figure 20:
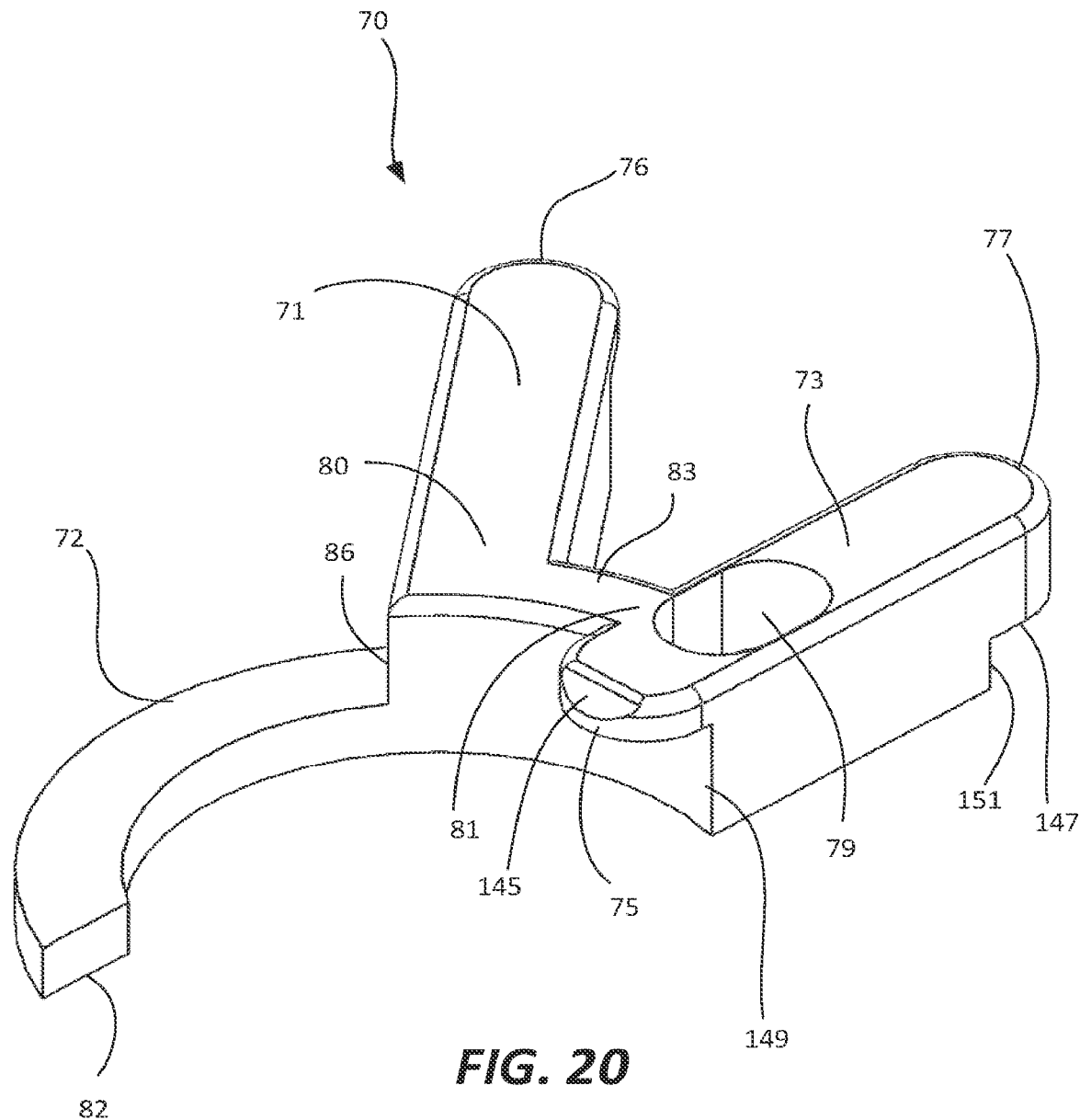
FIG. 20 is a perspective view diagram illustrating an angled three hole locking clip in accordance with at least one embodiment.

FIG. 20 is a perspective view diagram illustrating an angled three hole locking clip in accordance with at least one embodiment. FIG. 20 illustrates elements described above and allows their relationships and relative elevations to be seen in context. As shown, retention portion 72 can be of a lower profile than other portions, such as first substantially straight portion 71, connective portion 83, and second substantially straight portion 73, allowing retention portion 72 to be placed in a captive relationship with an undercut cavity defined in a plate in which the angled three hole locking clip may be installed. The captive relationship can maintain angled three hole locking clip 70 in the plate in which it may be installed, avoiding the potential for small loose parts.

In accordance with at least one embodiment, a locking clip is provided for retaining a fastener in a bone fixation plate. The locking clip comprises a flexure member and a body member coupled to the flexure member. The example illustrated in FIG. 20 includes a flexure member comprising retention portion 72. That example further includes a first body member comprising first substantially straight portion 71 and a second body member comprising second substantially straight portion 73. A body member comprises a locking tab. In the example of FIG. 20, the first body member comprises first locking tab 76, and the second body member comprises second locking tab 75 and third locking tab 77. A locking tab is configured to provide an axial limitation to motion of the fastener in a non-rotationally-ratcheting manner. The flexure member resiliently flexible to permit displacement of the locking tab to allow passage of a fastener head of the fastener. Other examples of flexure members and body members can be seen in other FIGs. described herein illustrating examples of a locking clip.

Figure 21:
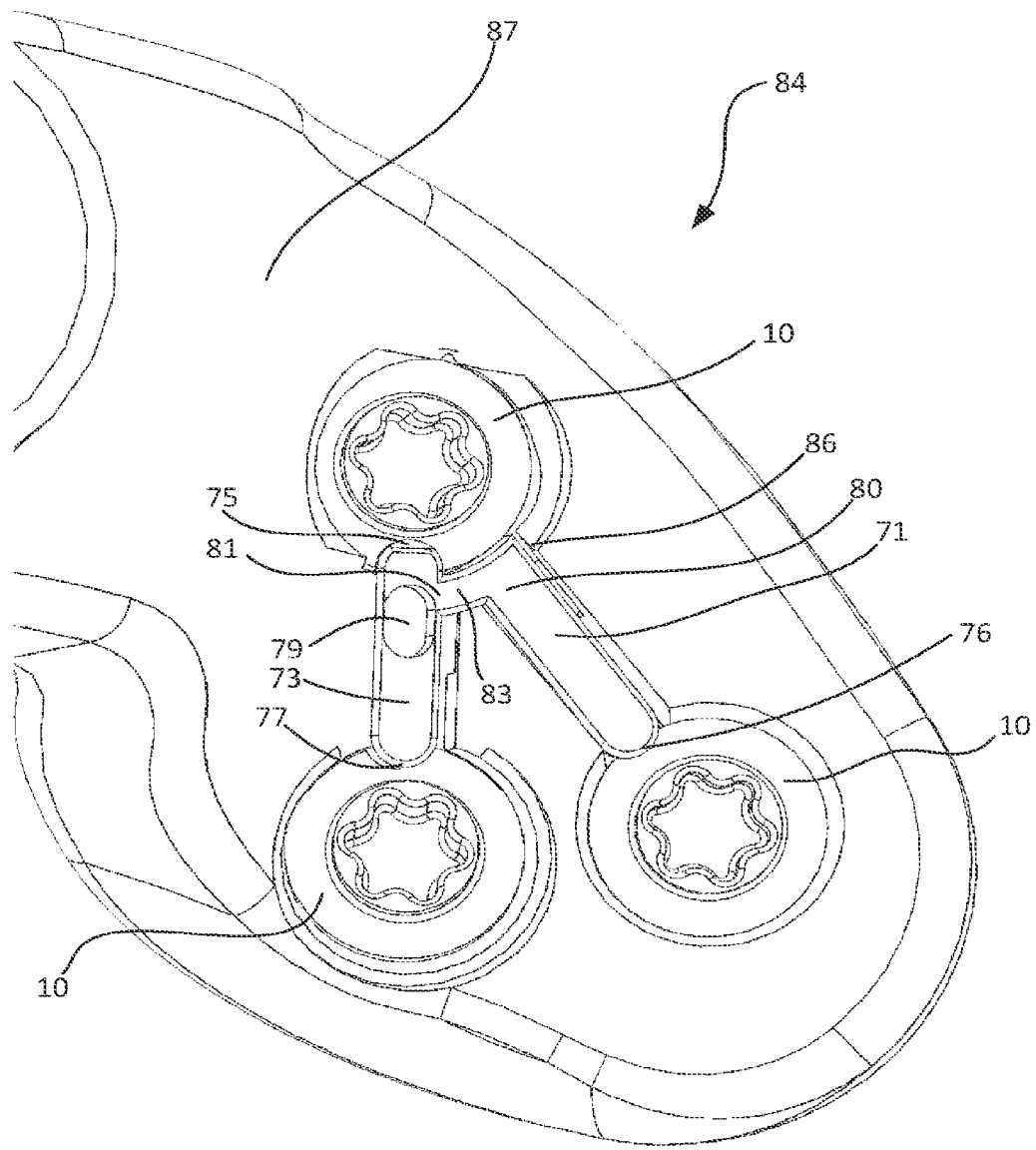
FIG. 21 is a plan view diagram illustrating a plate assembly incorporating an angled three hole locking clip in accordance with at least one embodiment.

FIG. 21 is a plan view diagram illustrating a plate assembly incorporating an angled three hole locking clip in accordance with at least one embodiment. Plate assembly 84 comprises plate 87 in which angled three hole locking clip 70 may be installed. Locking tab 75 retains a screw 10, while locking tab 76 retains another screw 10, and locking tab 77 retains yet another screw 10.

Figure 22:
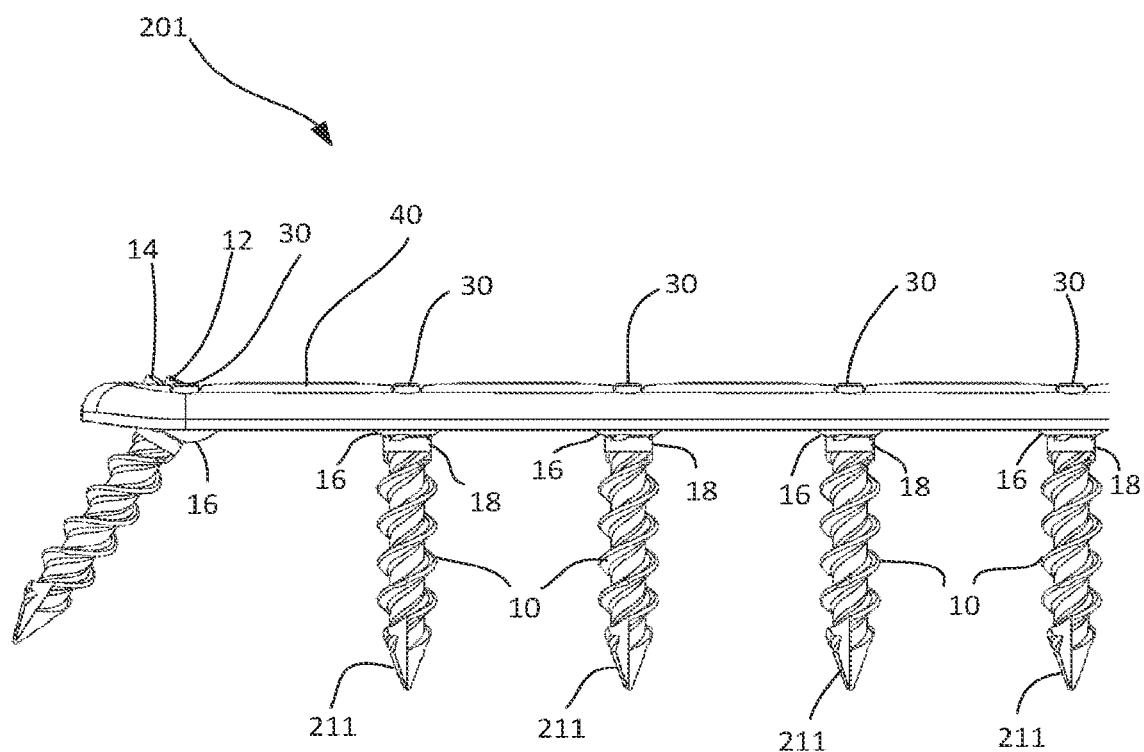
FIG. 22 is a side elevation view diagram illustrating a plate assembly incorporating locking clips with installed screws in accordance with at least one embodiment.

FIG. 22 is a side elevation view diagram illustrating a plate assembly incorporating locking clips with installed screws in accordance with at least one embodiment. Plate assembly 201 comprises an orthopedic plate 40 and a plurality of screws 10. Orthopedic plate 40 can have installed in it a plurality of clamps 30. Clamps 30, in the form of locking clips, retain screws 10 and prevent screws 10 from backing out once installed. Clamps 30 can comprise locking tabs having underside surfaces to retain screws 10. Screws 10 have an upper end surface 12, which may define, for example, a cavity for engagement with a screwdriver, for example, a multi-lobular cavity. Screws 10 also have an annular ledge surface 14, which may be at the same level as upper end surface 12 or at a more distal level than upper end surface 12. Ledge surface 14 provides an upward facing annular ledge that can bear against the underside surface of a locking tab to allow the locking tab to prevent the fastener from backing out. Screws 10 can have heads with convexly curved distal surfaces 116, such as a hemispherical distal surface. The convexly curved distal surfaces 116 of screws 10 can bear upon concavely curved surfaces surrounding holes within orthopedic plate 40, allowing screws 10 to swivel within orthopedic plate 40 to allow a wide range of angles of screws 10 relative to orthopedic plate 40. Screws 10 may comprise a shaft 18, which may comprise one or more threaded portions and zero or more unthreaded portions. Screws 10 may be configured with self-drilling heads 211 to allow screws 10 to drill and tap their own holes without the need for separate drilling and tapping operations.

Figure 23:
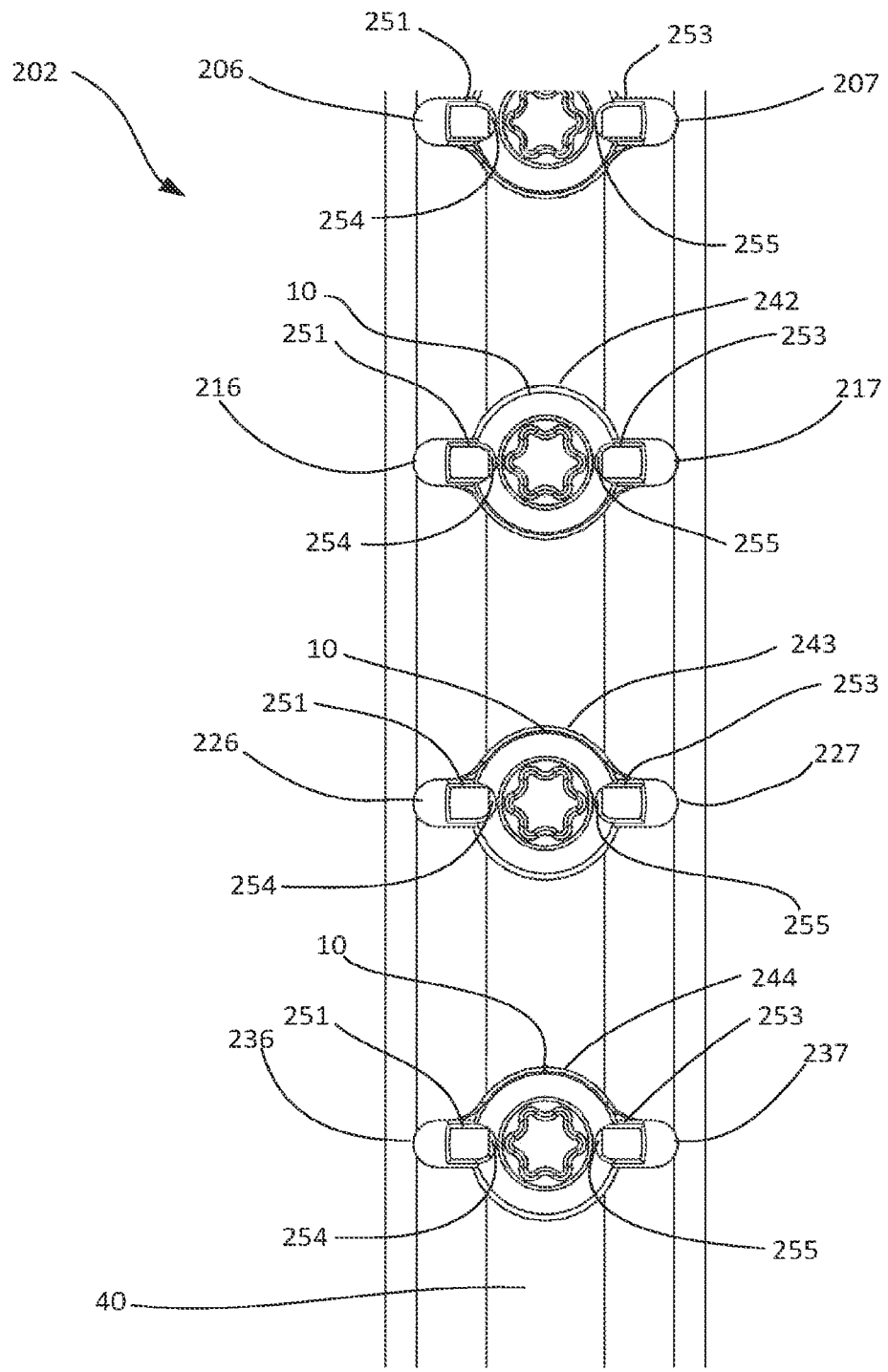
FIG. 23 is a plan view diagram illustrating a plate assembly incorporating locking clips with installed screws in accordance with at least one embodiment.

FIG. 23 is a plan view diagram illustrating a plate assembly incorporating locking clips with installed screws in accordance with at least one embodiment. Plate assembly 202 comprises orthopedic plate 40. Locking clips can be installed in orthopedic plate 40. The locking clips retain screws 10 to prevent the screws 10 from backing out once the screws are installed. Each locking clip comprises a first substantially straight portion 251 and a second substantially straight portion 253. The first substantially straight portion 251 can have a first locking tab 254. The second substantially straight portion 243 can have a second locking tab 255. Locking tabs 254 and 255 cooperate to retain the heads of screws 10 within orthopedic plate 40.

Cavities are defined in orthopedic plate 40 to retain the locking clips. The cavities include a circular cavity, such as circular cavities 242, 243, and 244. Each of the circular cavities can define a cylindrical portion. An arcuate undercut cavity can be defined adjacent to the cylindrical portion to house a retention portion or connective portion of a locking clip, facilitating retention of the locking clip in orthopedic plate 40. The arcuate undercut cavity can open, on one or both ends, into one or more cavities defined in orthopedic plate 40 to accept one or more substantially straight portions of the locking clip. For example, for one locking clip, cavity 206 is defined to accept first substantially straight portion 251, and cavity 207 is defined to accept second substantially straight portion 253. As another example, for another locking clip, cavity 216 is defined to accept first substantially straight portion 251, and cavity 217 is defined to accept second substantially straight portion 253. As yet another example, for yet another locking clip, cavity 226 is defined to accept first substantially straight portion 251, and cavity 227 is defined to accept second substantially straight portion 253. As a further example, for a further locking clip, cavity 236 is defined to accept first substantially straight portion 251, and cavity 237 is defined to accept second substantially straight portion 253.

Figure 24:
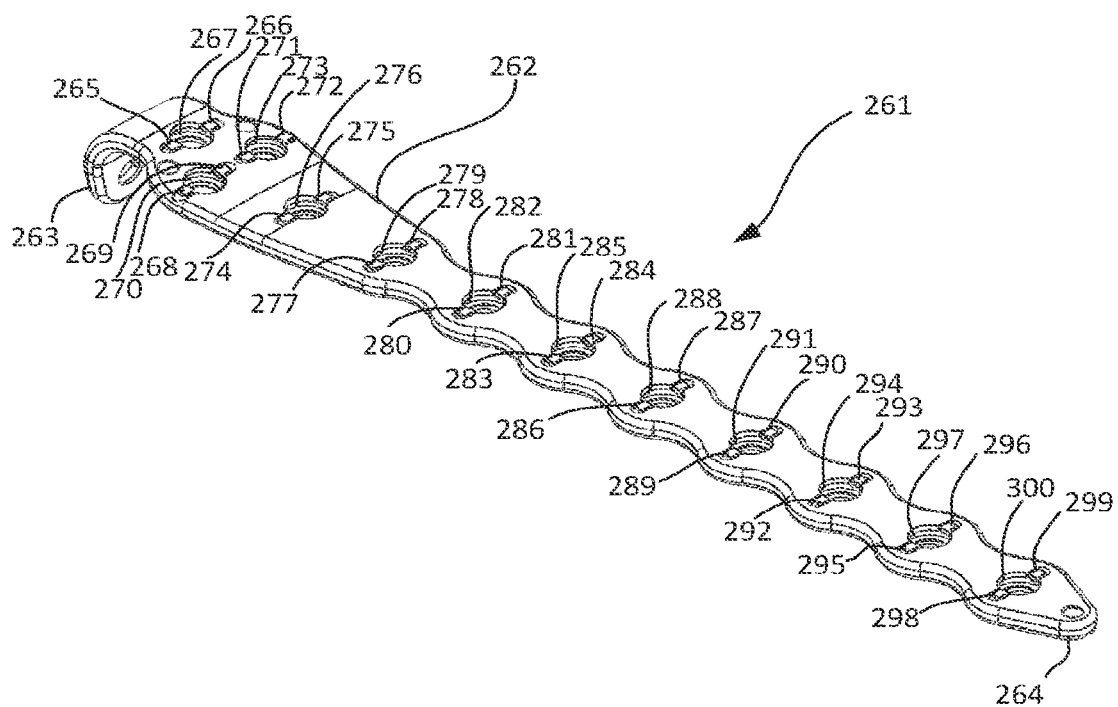
FIG. 24 is a perspective view diagram illustrating a plate assembly incorporating locking clips in accordance with at least one embodiment.

FIG. 24 is a perspective view diagram illustrating a plate assembly incorporating locking clips in accordance with at least one embodiment. Plate assembly 261 comprises plate 262 in which a plurality of locking clips can be installed. Plate 262 extends from a curved end 263 to a straight end 264. A first locking clip may be installed near curved end 263 and comprises first substantially straight portion 265, connective portion 267, and second substantially straight portion 266. A second locking clip and third locking clip can be installed in a side-by-side configuration. The second locking clip comprises first substantially straight portion 268, connective portion 270, and second substantially straight portion 269. The third locking clip comprises first substantially straight portion 271, connective portion 273, and second substantially straight portion 272. A fourth locking clip comprises first substantially straight portion 274, connective portion 276, and second substantially straight portion 275. A fifth locking clip comprises first substantially straight portion 277, connective portion 279, and second substantially straight portion 278. A sixth locking clip comprises first substantially straight portion 280, connective portion 282, and second substantially straight portion 281. A seventh locking clip comprises first substantially straight portion 283, connective portion 285, and second substantially straight portion 284. An eighth locking clip comprises first substantially straight portion 286, connective portion 288, and second substantially straight portion 287. A ninth locking clip comprises first substantially straight portion 289, connective portion 291, and second substantially straight portion 290. A tenth locking clip comprises first substantially straight portion 292, connective portion 294, and second substantially straight portion 293. An eleventh locking clip comprises first substantially straight portion 295, connective portion 297, and second substantially straight portion 296. A twelfth locking clip may be installed near straight end 264 and comprises first substantially straight portion 298, connective portion 300, and second substantially straight portion 299.

Figure 25:
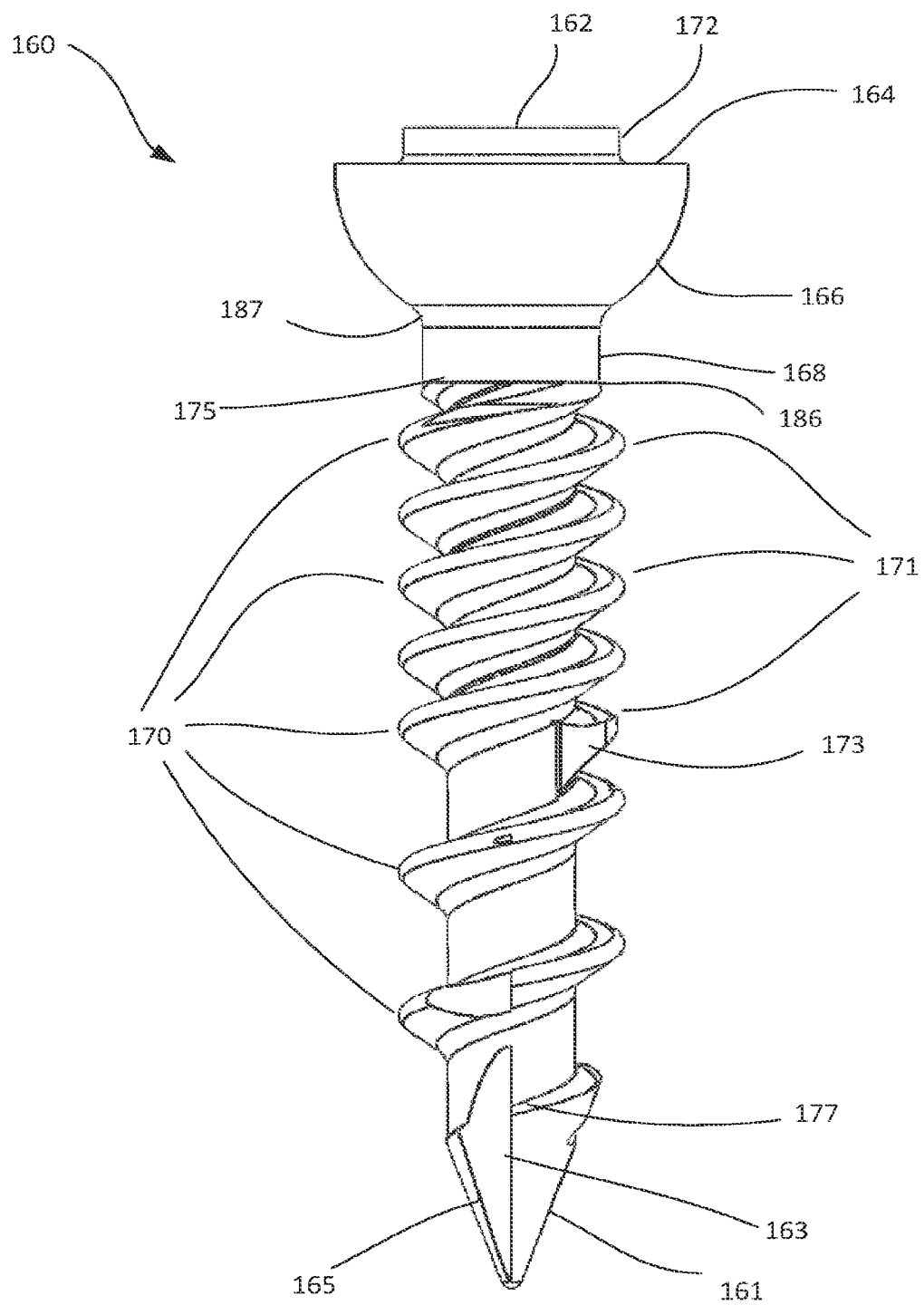
FIG. 25 is an elevation view diagram illustrating a fully threaded axially displaced double-lead threaded screw in accordance with at least one embodiment.

FIG. 25 is an elevation view diagram illustrating a fully threaded axially displaced double-lead threaded screw in accordance with at least one embodiment. The screw 160 of FIG. 25 may be used, for example, as a cancellous and cortical screw, for engaging, with its different types of threads over different portions of the length of its shaft, different types of bone, such as cancellous bone and cortical bone. The screw 160 of FIG. 25 comprises a self-drilling tip 161. The self-drilling tip can have a cutting edge 163 and a following edge 165 that define an angular cavity in self-drilling tip 161 that can serve as a straight flute to expose cutting edge 163.

Screw 160 comprises single lead wide pitch thread 170 that begins at thread starting point 177 and continues to thread ending point 186. As thread starting point 177 can lie along cutting edge 163, self-drilling tip 161 can serve as a self-tapping tip as well as a self-drilling tip. Self-drilling tip 161 can both drill a hole for the shaft of screw 160 and cut a helical groove for single lead wide pitch thread 170 to engage. Along a distal portion of the shaft of screw 160, single lead wide pitch thread 170 form a single helix where the pitch is sufficient to accommodate the width of an additional thread of the same pitch between adjacent turns of single lead wide pitch thread 170. However, over the distal portion, the additional thread is absent. Instead, the cylindrically helical unthreaded portion of the shaft exists between adjacent turns of the single lead wide pitch thread 170 over the distal portion of screw 160.

Above the distal portion of screw 160, a thread-cutting edge 173 of additional wide pitch thread 171 lies between adjacent turns of single lead wide pitch thread 170. Additional wide pitch thread 171 forms a helix whose turns lie between the turns of single lead wide pitch thread 170 along the same axis as single lead wide pitch thread 170. Thus, alternations of single lead wide pitch thread 170 and additional wide pitch thread 171 lie along a proximal portion of screw 160 above the distal portion of screw 160. Single lead wide pitch thread 170 continues until thread termination 186. Additional wide pitch thread 171 continues until thread termination 175. In the illustrated embodiment, thread termination 186 and thread termination 175 lie at the same distance along the shaft of screw 160 (e.g., at the same distance from annular ledge 164, and, e.g., at the same distance from self-drilling tip 161).

Proximal to (e.g., above) the proximal portion of the shaft of screw 160 where single lead wide pitch thread 170 and additional wide pitch thread 171 are located, a cylindrical portion 168 of screw 160 may be located. In accordance with other embodiments, cylindrical portion 168 may be omitted. Proximal to (e.g., above) cylindrical portion 168 of screw 160 or the proximal portion of the shaft of screw 160, a transitional portion 187 transitioning to a convexly curved distal portion 166 of a head of screw 160 may be located. In accordance with other embodiments, transitional portion 187 may be omitted. Proximal to (e.g., above) transitional portion 187 or cylindrical portion 168 or the proximal portion of the shaft of screw 160, convexly curved distal portion 166 of the head of screw 160 is located. An annular ledge 164 is defined at the proximal edge of convexly curved distal portion 166 of the head of screw 160. In the illustrated embodiment, a cylindrical riser 172 lies proximal to (e.g., above) annular ledge 164, and cylindrical riser 172 rises to an upper end surface 162. Upper end surface 162 may be planar. A cavity may be defined in upper end surface 162 to accept a screwdriver for driving screw 160 into and out of a material, such as bone. The cavity defined in upper end surface 162 may, for example, be multi-lobular, polygonal, or multi-slotted. Annular ledge 164 may be at the same level as upper end surface 162, obviating cylindrical riser 172, or at a more distal level than upper end surface 162 by virtue of the translational displacement along the axis of screw 160 provided by cylindrical riser 172.

The absence of projections, such as ratchet teeth, extending outwardly from cylindrical riser 172 helps prevent a locking clip engaging annular ledge 164 from acting as a pawl and inhibiting rotation of screw 160. As rotation of screw 160 does not result in rotational ratcheting, screw 160 can cooperate with a locking clip having a locking tab to ensure the locking tab is configured to provide an axial limitation to motion of the fastener in a non-rotationally-ratcheting manner. The axial limitation is provided by the locking tab being displaced outwardly from the axis of screw 160 by a wedging action of convexly curved distal portion 166 of the head of screw 160 as the screw is driven into bone. As screw 160 is driven further into bone, the locking clip clears convexly curved distal portion 166 and the radially relieved annular gap defined by annular ledge 164 allows the locking tab to snap into the gap.

By constructing the locking clip of a material exhibiting elasticity, the locking clip provides a spring feature to bias the locking clip toward its neutral form when displaced by force, such as the wedging force of convexly curved distal portion 166. Such elasticity of the material of the locking clip allows the locking clip to be resiliently flexible, as flexure of the locking clip can occur but the locking clip will tend to spring back to its neutral form when a displacing force ceases. When screw 160 is driven sufficiently to clear convexly curved distal portion 166, and the spring feature causes the spring clip to snap back to its neutral form over annular ledge 164, at least a portion of the energy stored according to the spring feature of the locking clip can be released in the form of an impulse of mechanical energy. The impulse of mechanical energy can result in some momentary resonance of the mechanical structures, such as the locking clip, screw 160, or the locking plate, to produce a brief mechanical vibration. The brief mechanical vibration may interact with air molecules to produce a brief sound, such as a click. Thus, the snapping action can provide an audible indication, a tactile indication, or both an audible and tactile indication that the locking clip has engaged screw 160 to provide axial limitation of motion of screw 160.

The axial limitation of motion is provided by at least one locking tab of a locking clip situated, in an engaged relationship with screw 160, to bear upon annular ledge 164 of screw 160. Depending on an amount of micromotion between screw 160 and the bone into which it is driven that may be desired or a preference to avoid such micromotion, an extent to which the at least one locking tab of the locking clip bears upon annular ledge 164 of screw 160 can be controlled. As one example, screw 160 can be driven past the point at which the at least one locking tab of the locking clip engages annular ledge 164 to allow for some amount of micromotion, as screw 160 can be provided freedom to back out slightly until annular ledge 164 of screw 160 solidly bears upon annular ledge 164. As another example, screw 160 can be driven to the point at which the at least one locking tab engages annular ledge 164 but no further, resulting in the at least one locking tab resting on but not bearing forcibly against annular ledge 164. As a further example, screw 160 can be driven to the point at which the at least one locking tab engages annular ledge 164 and then driven in reverse to cause the at least one locking tab to forcibly bear against annular ledge 164, effectively securing screw 160 in a fixed relationship to the locking clip and the plate in which it is installed and inhibiting micromotion.

As the at least one locking tab bears against a portion of screw 160 in a direction parallel to the axis of screw 160, the at least one locking tab provides axial limitation to the motion of screw 160. As the at least one locking tab does not bear against a portion of screw 160 in a direction tangential to the axis of screw 160, as would be the case with a rotational ratchet and pawl arrangement, the at least one locking tab does not provide direct rotational limitation of the motion of screw 160. Rather, any effective rotational limitation to the motion of screw 160 provided by the at least one locking tab is entirely indirect, solely as a consequence of the ramped nature of the screw threads of screw 160, and the direct limitation to the motion of screw 160 is an axial limitation.

The non-rotationally-ratcheting manner of providing axial limitation to the motion of screw 160, the selectable allowance or inhibition of micromotion, and the audible indication, tactile indication, or audible and tactile indication of engagement of a locking clip with screw 160 are described with respect to screw 160 but are not limited solely to screw 160 and a locking clip used in conjunction with screw 160. Rather, such features may be provided with other embodiments of screws and clips as disclosed herein, including, but not limited to, specific illustrated embodiments of screws and clips.

As thread starting point 177 forms a single lead and thread starting point 177 and thread cutting edge 173 together form a double lead, screw 160 is a single lead screw along the distal portion of its shaft and is a double lead screw along the proximal portion of its shaft. The single lead wide pitch thread 170 can provide compatibility with less dense materials, such as cancellous bone, while the combination of the single lead wide pitch thread 170 and the additional wide pitch thread 171 can provide compatibility with denser materials, such as cortical bone. Thus, screw 160 can provide cancellous bone and cortical bone compatibility in a single screw.

Figure 26:
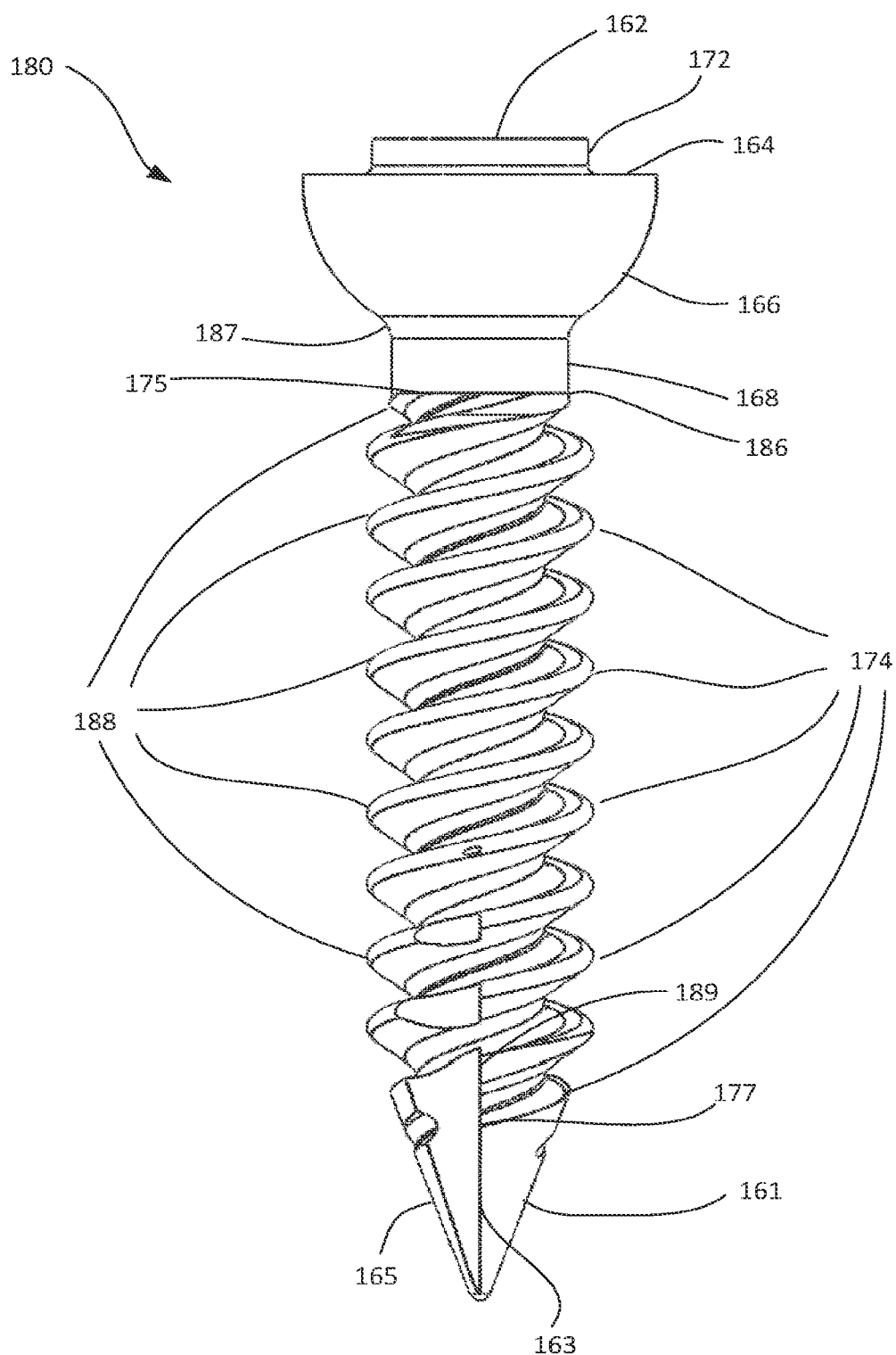
FIG. 26 is an elevation view diagram illustrating a fully threaded cortical screw in accordance with at least one embodiment.

FIG. 26 is an elevation view diagram illustrating a fully threaded cortical screw in accordance with at least one embodiment. The screw 180 of FIG. 26 may be used, for example, as a cortical screw, for engaging a uniform type of material, such as cortical bone, along the length of its shaft. The screw 180 of FIG. 26 comprises a self-drilling tip 161. The self-drilling tip can have a cutting edge 163 and a following edge 165 that define an angular cavity in self-drilling tip 161 that can serve as a straight flute to expose cutting edge 163.

Screw 180 comprises wide pitch thread 174 that begins at thread starting point 177 and continues to thread ending point 186 and wide pitch thread 188 that begins at thread starting point 189 and continues to thread ending point 175. As thread starting point 177 and thread starting point 189 can lie along cutting edge 163, self-drilling tip 161 can serve as a self-tapping tip as well as a self-drilling tip. Self-drilling tip 161 can both drill a hole for the shaft of screw 180 and cut a first helical groove for wide pitch thread 174 to engage and a second helical groove for wide pitch thread 188 to engage. Wide pitch thread 174 and wide pitch thread 188 form two helices of the same pitch around the same axis of the shaft of screw 180 but with different thread timing. As illustrated, the thread timing can be 180 degrees, maintaining diametrical separation of the two helices. Thus, alternations of wide pitch thread 174 and wide pitch thread 188 lie along substantially the entire shaft of screw 180. Wide pitch thread 174 continues until thread termination 186. Wide pitch thread 188 continues until thread termination 175. In the illustrated embodiment, thread termination 186 and thread termination 175 lie at the same distance along the shaft of screw 180 (e.g., at the same distance from annular ledge 164, and, e.g., at the same distance from self-drilling tip 161).

Proximal to (e.g., above) the portion of the shaft of screw 180 where wide pitch thread 174 and wide pitch thread 188 are located, a cylindrical portion 168 of screw 180 may be located. In accordance with other embodiments, cylindrical portion 168 may be omitted. Proximal to (e.g., above) cylindrical portion 168 of screw 180 or the proximal portion of the shaft of screw 180, a transitional portion 187 transitioning to a convexly curved distal portion 166 of a head of screw 180 may be located. In accordance with other embodiments, transitional portion 187 may be omitted. Proximal to (e.g., above) transitional portion 187 or cylindrical portion 168 or the proximal portion of the shaft of screw 180, convexly curved distal portion 166 of the head of screw 180 is located. An annular ledge 164 is defined at the proximal edge of convexly curved distal portion 166 of the head of screw 180. In the illustrated embodiment, a cylindrical riser 172 lies proximal to (e.g., above) annular ledge 164, and cylindrical riser 172 rises to an upper end surface 162. Upper end surface 162 may be planar. A cavity may be defined in upper end surface 162 to accept a screwdriver for driving screw 180 into and out of a material, such as bone. The cavity defined in upper end surface 162 may, for example, be multi-lobular, polygonal, or multi-slotted. Annular ledge 164 may be at the same level as upper end surface 162, obviating cylindrical riser 172, or at a more distal level than upper end surface 162 by virtue of the translational displacement along the axis of screw 180 provided by cylindrical riser 172.

As thread starting point 177 and thread starting point 189 together form a double lead, screw 180 is a double lead screw along substantially the entire length of its shaft. The wide pitch thread 174 interleaved with wide pitch thread 188 can provide compatibility with denser materials, such as cortical bone. Thus, screw 180 can provide cortical bone compatibility along substantially its entire length.

Figure 27:
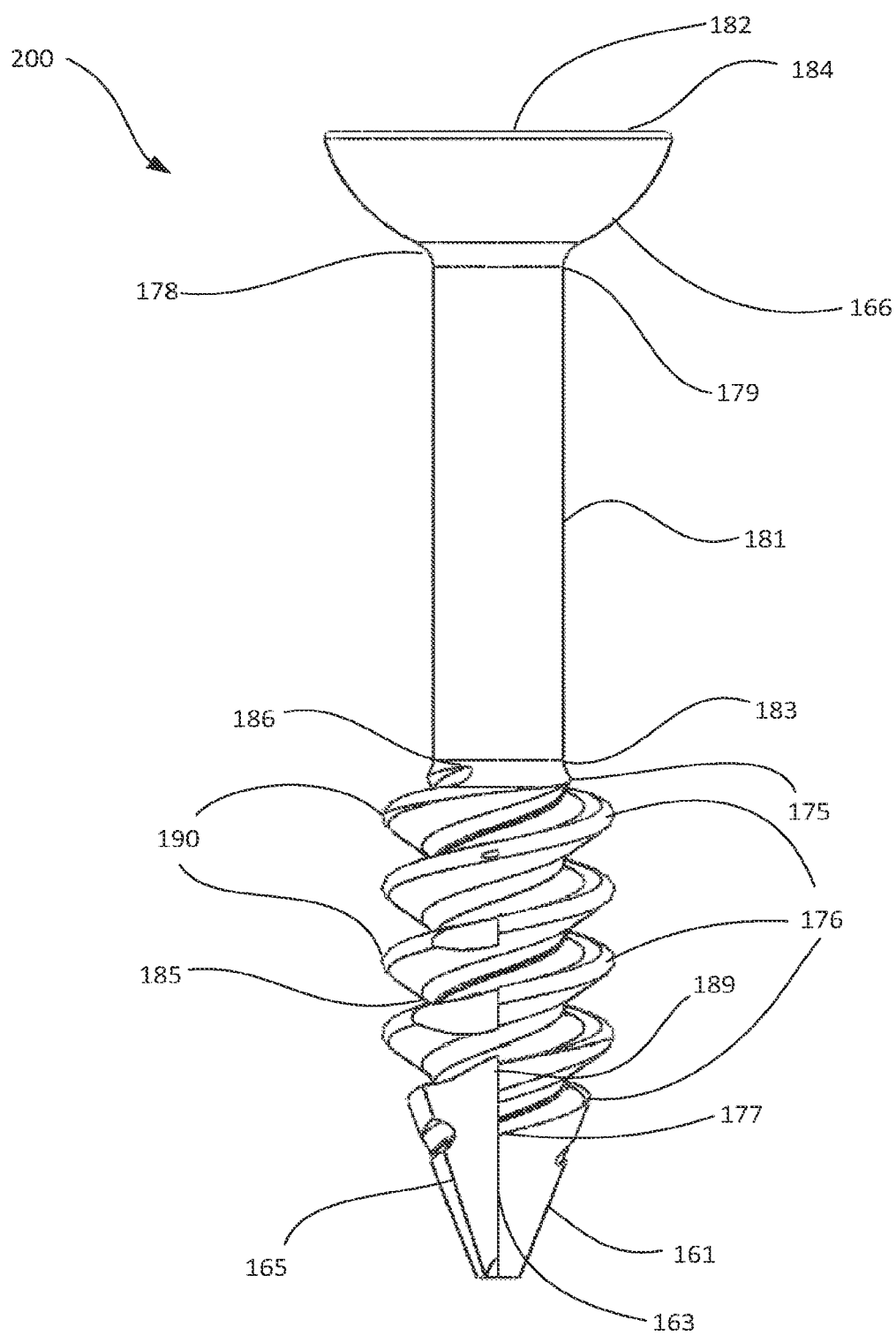
FIG. 27 is an elevation view diagram illustrating a partially threaded cortical screw in accordance with at least one embodiment.

FIG. 27 is an elevation view diagram illustrating a partially threaded cortical screw in accordance with at least one embodiment. The screw 200 of FIG. 27 may be used, for example, as a cortical screw, for engaging a uniform type of material, such as cortical bone, along a threaded portion 185 of the length of its shaft. The screw 200 of FIG. 27 comprises a self-drilling tip 161. The self-drilling tip can have a cutting edge 163 and a following edge 165 that define an angular cavity in self-drilling tip 161 that can serve as a straight flute to expose cutting edge 163.

Screw 200 comprises wide pitch thread 176 that begins at thread starting point 177 and continues to thread ending point 186 and wide pitch thread 190 that begins at thread starting point 189 and continues to thread ending point 175. As thread starting point 177 and thread starting point 189 can lie along cutting edge 163, self-drilling tip 161 can serve as a self-tapping tip as well as a self-drilling tip. Self-drilling tip 161 can both drill a hole for the shaft of screw 200 and cut a first helical groove for wide pitch thread 176 to engage and a second helical groove for wide pitch thread 190 to engage. Wide pitch thread 176 and wide pitch thread 190 form two helices of the same pitch around the same axis of the shaft of screw 200 but with different thread timing. As illustrated, the thread timing can be 180 degrees, maintaining diametrical separation of the two helices. Thus, alternations of wide pitch thread 176 and wide pitch thread 190 lie along a distal portion shaft of screw 200. Wide pitch thread 176 continues until thread termination 186. Wide pitch thread 190 continues until thread termination 175. In the illustrated embodiment, thread termination 186 and thread termination 175 lie at the same distance along the shaft of screw 200 (e.g., at the same distance from annular ledge 164, and, e.g., at the same distance from self-drilling tip 161).

Proximal to (e.g., above) the distal portion of the shaft of screw 200 where wide pitch thread 176 and wide pitch thread 190 are located, an unthreaded cylindrical portion 181 of the shaft of screw 200 may be located. An annular boundary 193 lies between the distal portion of the shaft of screw 200 where wide pitch thread 176 and wide pitch thread 190 are located and unthreaded cylindrical portion 181. Proximal to (e.g., above) unthreaded cylindrical portion 181 of screw 200, a transitional portion 178 transitioning to a convexly curved distal portion 166 of a head of screw 200 may be located. Transitional portion 178 may be connected to unthreaded cylindrical portion 181 at annular junction 179. In accordance with other embodiments, transitional portion 178 may be omitted. Proximal to (e.g., above) transitional portion 178 or unthreaded cylindrical portion 181, convexly curved distal portion 166 of the head of screw 180 is located. An annular ledge is defined at the proximal edge of convexly curved distal portion 166 of the head of screw 200. In the illustrated embodiment, the annular ledge 184 lies at the same level as upper end surface 182. A cavity may be defined in upper end surface 182 to accept a screwdriver for driving screw 200 into and out of a material, such as bone. The cavity defined in upper end surface 182 may, for example, be multi-lobular, polygonal, or multi-slotted. In accordance with another embodiment, a cylindrical riser lies proximal to (e.g., above) annular ledge 184, and the cylindrical riser rises to an upper end surface 182. Upper end surface 182 may be planar. Annular ledge 184 may be at a more distal level than upper end surface 182 by virtue of the translational displacement along the axis of screw 200 provided by cylindrical riser 172.

As thread starting point 177 and thread starting point 189 together form a double lead, screw 200 is a double lead screw along substantially the entire length of the threaded portion 185 of its shaft. The wide pitch thread 174 interleaved with wide pitch thread 188 can provide compatibility with denser materials, such as cortical bone. Thus, screw 200 can provide cortical bone compatibility along substantially the entire length of the threaded portion 185 of its shaft.

In accordance with other embodiments, threaded portion 185 may be threaded with a single lead thread of wide pitch, for example, to provide compatibility with less dense material, such as cancellous bone. As another example, threaded portion 185 may span a more proximal portion of the shaft of screw 200. As another example, multiple threaded portions may exist along different portions of the shaft of screw 200. As examples, two or more threaded portions both may be single lead threads or double lead threads, or one threaded portion may have a single lead thread while another threaded portion may have a double lead thread. The pitch of two or more threaded portions may be the same or different. As examples, a distal threaded portion may have a greater pitch and a proximal threaded portion may have a lesser pitch to provide tension along the shaft of screw 200 or a distal threaded portion may have a lesser pitch and a proximal threaded portion may have a greater pitch to provide compression along the shaft of screw 200.

Figure 28:
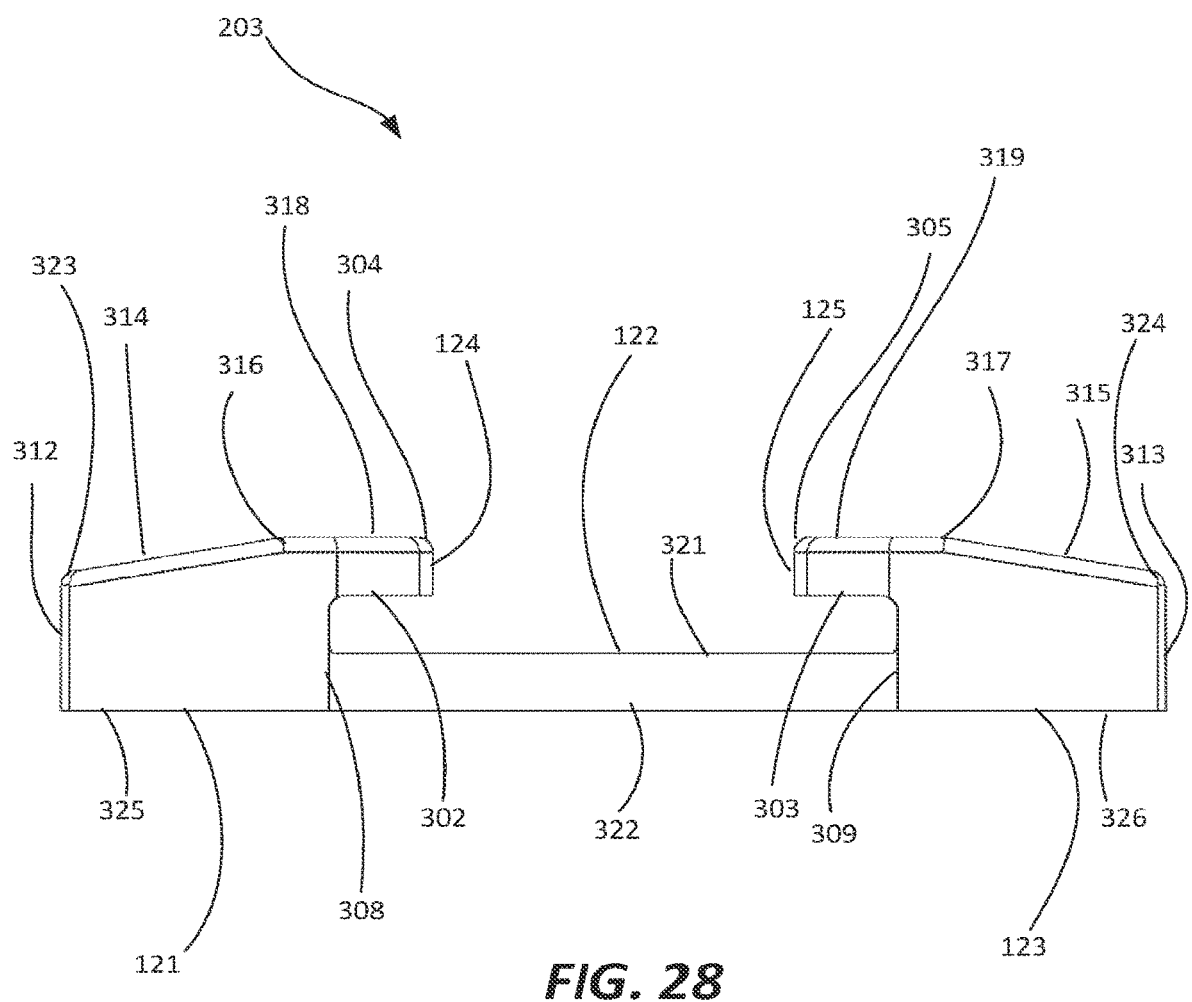
FIG. 28 is a front elevation view diagram illustrating a single hole locking clip with clip tool engagement cavities in accordance with at least one embodiment.

FIG. 28 is a front elevation view diagram illustrating a single hole locking clip with clip tool engagement cavities in accordance with at least one embodiment. Single hole locking clip 203 comprises first substantially straight portion 121, connective portion 122, and second substantially straight portion 123. First substantially straight portion 121 extends radially outward from locking tab 124 at its inner end to outer face 312 at its outer end. Second substantially straight portion 123 extends radially outward from locking tab 125 at its inner end to outer face 313 at its outer end.

Locking tab 124 has an upper surface 318 and an underside surface 302. Locking tab 125 has an upper surface 319 and an underside surface 303. Connective portion 122 has an upper surface 321 and a lower surface 322. As shown in the illustrated embodiment, the lower surface 322 of connective portion 122 may be at substantially the same level as lower surface 325 of first substantially straight portion 121 and lower surface 326 of second substantially straight portion 123. As upper surface 321 of connective portion 122 can be at a lower level than upper surface 318 of locking tab 124 and upper surface 319 of locking tab 125, connective portion 122 can be situated low enough and can have a height thin enough to allow connective portion 122 to be recessed within a cavity undercut from the interior of a circular cavity for receiving the head of a screw within an orthopedic plate.

Locking tab 124 may or may not have a chamfered or radiused upper inward edge 304, which can act as a wedge to cooperate with a conical or curved distal portion of a head of a screw to laterally displace locking tab 124 to allow the head of the screw to pass by locking tab 124. Locking tab 125 may or may not have a chamfered or radiused upper inward edge 305, which can act as a wedge to cooperate with a conical or curved distal portion of a head of a screw to laterally displace locking tab 125 to allow the head of the screw to pass by locking tab 125. After the head of the screw has passed below locking tabs 124 and 125, locking tabs 124 and 125 can return to their neutral positions as urged by the flexure of connective portion 122.

Underside surface 302 of locking tab 124 intersects vertical wall 308 of first substantially straight portion 121. Underside surface 303 of locking tab 125 intersects vertical wall 309 of second substantially straight portion 123. Once the head of a screw has passed below locking tabs 124 and 125, the head of the screw can be retained between vertical wall 308 of first substantially straight portion 121 and vertical wall 309 of second substantially straight portion 123, beneath underside surface 302 of locking tab 124 and underside surface 303 of locking tab 125, within the inner radius of connective portion 122.

The upper surface 314 of first substantially straight portion 121 can be angled downward in an outward direction. As shown in the embodiment of FIG. 28, upper surface 318 of locking tab 124 can be level (e.g., parallel to lower surface 325 of first substantially straight portion 121 until edge 316, beyond which in an outward direction upper surface 314 of first substantially straight portion 121 slopes downward, reducing the thickness of first substantially straight portion 121 in the radially outward direction. Upper surface 314 meets outer face 312 of first substantially straight portion 121 along edge 323. Edge 323 may be chamfered or radiused.

The upper surface 315 of second substantially straight portion 123 can be angled downward in an outward direction. As shown in the embodiment of FIG. 28, upper surface 319 of locking tab 125 can be level (e.g., parallel to lower surface 326 of second substantially straight portion 123 until edge 317, beyond which in an outward direction upper surface 315 of second substantially straight portion 123 slopes downward, reducing the thickness of second substantially straight portion 123 in the radially outward direction. Upper surface 315 meets outer face 313 of second substantially straight portion 123 along edge 324. Edge 324 may be chamfered or radiused.

Figure 29:
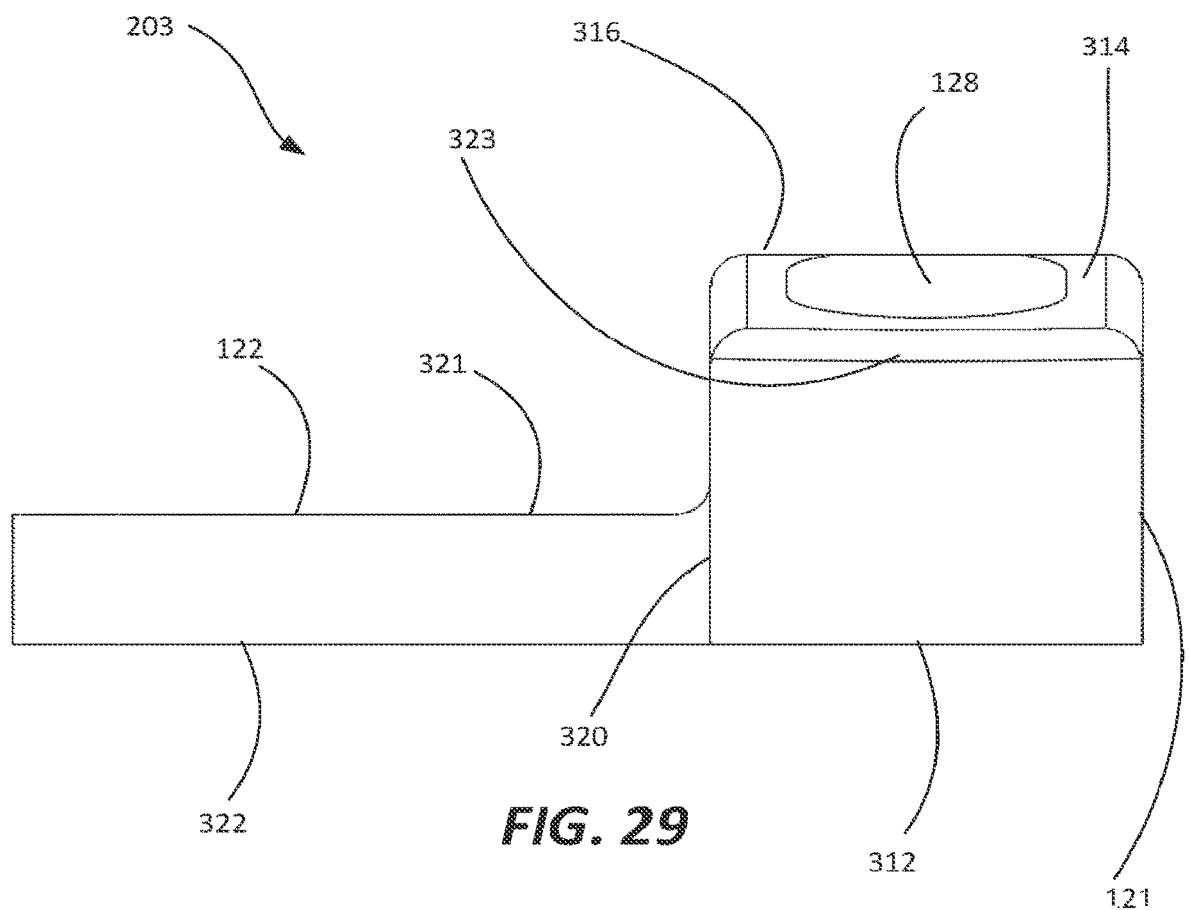
FIG. 29 is a side elevation view diagram illustrating a single hole locking clip with clip tool engagement cavities in accordance with at least one embodiment.

FIG. 29 is a side elevation view diagram illustrating a single hole locking clip with clip tool engagement cavities in accordance with at least one embodiment. FIG. 29 shows elements of single hole locking clip 203 as shown in FIG. 28. FIG. 29 also shows first clip tool engagement cavity 128 defined in first substantially straight portion 121. FIG. 29 further shown junction 320 between first substantially straight portion 121 and connective portion 122.

Figure 30:
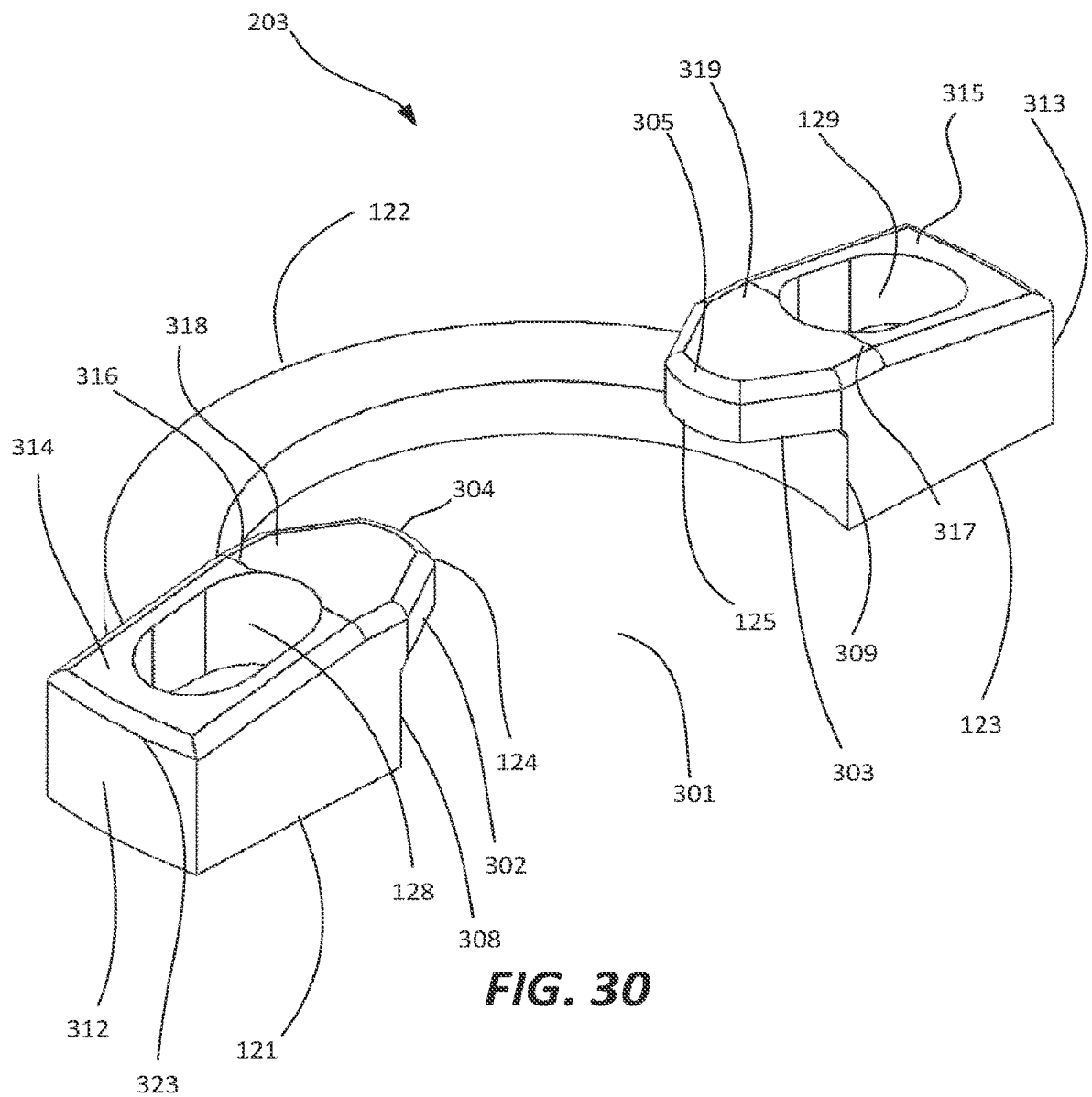
FIG. 30 is a perspective view diagram illustrating a single hole locking clip with clip tool engagement cavities in accordance with at least one embodiment.

FIG. 30 is a perspective view diagram illustrating a single hole locking clip with clip tool engagement cavities in accordance with at least one embodiment. FIG. 30 shows elements of single hole locking clip 203 as shown in FIGS. 28 and 29. FIG. 30 also shows second clip tool engagement cavity 129 defined in upper surface 315 of second substantially straight portion 123. First clip tool engagement cavity 128 as defined in upper surface 314 of first substantially straight portion 121 is also visible in FIG. 30. FIG. 30 further shows space 301 defined inside of the inner radius of connective portion 122 and between vertical wall 308 of first substantially straight portion 121 and vertical wall 309 of second substantially straight portion 123 beneath underside surface 302 of locking tab 304 and underside surface 303 of locking tab 305.

In accordance with at least one embodiment, a locking clip is provided for retaining a fastener in a bone fixation plate. The locking clip comprises a flexure member and a body member coupled to the flexure member. The example illustrated in FIG. 30 includes a flexure member comprising connective portion 122. That example further includes a first body member comprising first substantially straight portion 121 and a second body member comprising second substantially straight portion 123. A body member comprises a locking tab. In the example of FIG. 30, the first body member comprises locking tab 124, and the second body member comprises locking tab 125. A locking tab is configured to provide an axial limitation to motion of the fastener in a non-rotationally-ratcheting manner. The flexure member resiliently flexible to permit displacement of the locking tab to allow passage of a fastener head of the fastener. Other examples of flexure members and body members can be seen in other FIGs. described herein illustrating examples of a locking clip.

In accordance with at least one embodiment, a locking clip comprises a single locking tab for retaining a single fastener. In accordance with at least one embodiment, a locking clip comprises two locking tabs for retaining a single fastener. In accordance with at least one embodiment, a locking clip comprises at least a first locking tab for retaining a first fastener and at least a second locking tab for retaining a second fastener. In accordance with at least one embodiment, the locking clip comprises at least a first locking tab for retaining a first fastener, at least a second locking tab for retaining a second fastener, and at least a third locking tab for retaining a third fastener. In accordance with at least one embodiment, a flexure member is an arcuate flexure member. In accordance with at least one embodiment, a locking clip is configured to provide a discernable indication of the locking tab locking a fastener head selected from a group consisting of a tactile indication and an audible indication.

In accordance with at least one embodiment, a bone fixation plate assembly for receiving a fastener is provided. The bone fixation plate assembly comprises a bone fixation plate and a locking clip. The locking clip comprises a body member. The body member comprises a locking tab. The locking clip has a flexure member situated in a clip cavity of the plate. The locking tab is configured to provide an axial limitation to motion of the fastener in a non-rotationally-ratcheting manner. In accordance with at least one embodiment, the flexure member is resiliently flexible to permit displacement of the locking tab to allow passage of a fastener head of the fastener. In accordance with at least one embodiment, a clip tool engagement cavity is defined in the body member, wherein a side wall defining a lateral extent of the clip tool engagement cavity is configured to facilitate application of lateral force using a clip tool to translate the body member. In accordance with at least one embodiment, the clip cavity is defined peripheral to a fastener head cavity defined in the plate, the fastener head cavity configured to receive a fastener head of the fastener. In accordance with at least one embodiment, the flexure member is an arcuate flexure member. In accordance with at least one embodiment, the locking clip is configured to provide a discernable indication of the locking tab locking a fastener head selected from a group consisting of a tactile indication and an audible indication.

In accordance with at least one embodiment, a locking fastener assembly comprises a fastener having an exterior wedging surface of varying exterior diameter over a fastener wedging portion length and a locking ring having an interior wedging surface of varying interior diameter over a locking ring wedging surface length, the exterior wedging surface and the interior wedging surface adapted to radially expand the locking ring upon installation of the fastener. In accordance with at least one embodiment, the exterior wedging surface is a frustoconical exterior wedging surface. In accordance with at least one embodiment, the interior wedging surface is a frustoconical interior wedging surface. In accordance with at least one embodiment, the locking ring has a convexly curved exterior locking ring surface. In accordance with at least one embodiment, the convexly curved exterior locking ring surface is a partially spherical exterior surface. In accordance with at least one embodiment, the fastener comprises a flange of larger diameter than a largest diameter of the varying exterior diameter adjacent to the largest diameter of the varying exterior diameter of the exterior wedging surface. In accordance with at least one embodiment, the exterior wedging surface and the interior wedging surface have cooperative longitudinally features defined thereon to inhibit relative rotation.

FIGS. 31-35 illustrate an embodiment of a locking fastener assembly. The illustrated embodiment of the locking fastener assembly comprises a fastener having an exterior wedging surface of varying exterior diameter over a fastener wedging portion length and a locking ring having an interior wedging surface of varying interior diameter over a locking ring wedging surface length. The exterior wedging surface and the interior wedging surface are adapted to radially expand the locking ring upon installation of the fastener. In accordance with at least one embodiment, the exterior wedging surface is a frustoconical exterior wedging surface. In accordance with at least one embodiment, the interior wedging surface is a frustoconical interior wedging surface. In accordance with at least one embodiment, the locking ring has a convexly curved exterior locking ring surface. In accordance with at least one embodiment, the convexly curved exterior locking ring surface is a partially spherical exterior surface. In accordance with at least one embodiment, the fastener comprises a flange of larger diameter than a largest diameter of the varying exterior diameter adjacent to the largest diameter of the varying exterior diameter of the exterior wedging surface. In accordance with at least one embodiment, the exterior wedging surface and the interior wedging surface have cooperative longitudinally features defined thereon to inhibit relative rotation.

Figure 31:
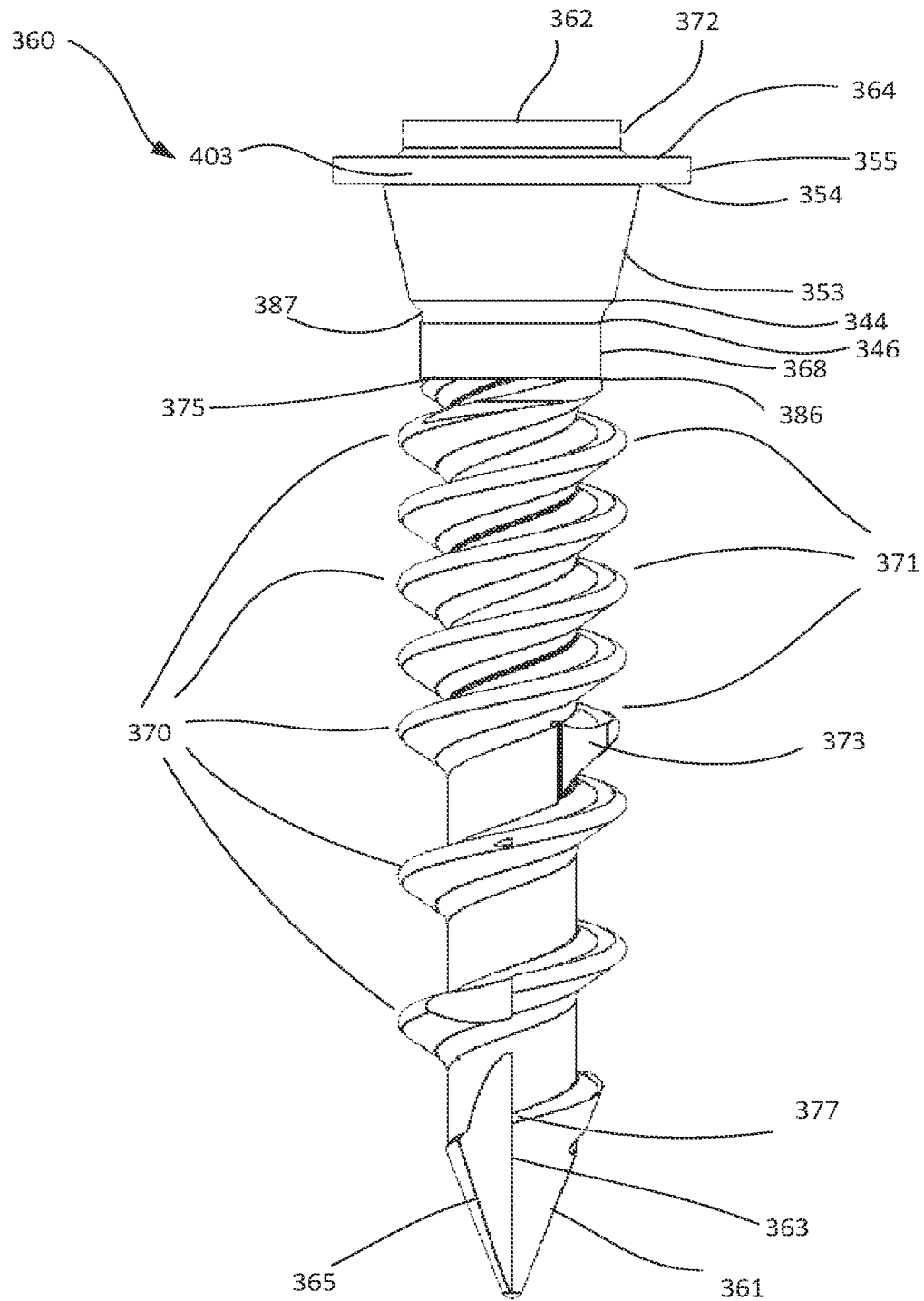
FIG. 31 is an elevation view diagram illustrating a screw for a locking screw assembly in accordance with at least one embodiment.

FIG. 31 is an elevation view diagram illustrating a screw for a locking screw assembly in accordance with at least one embodiment. Screw 360 is illustrated and described below as a fully threaded axially displaced double-lead threaded screw in accordance with at least one embodiment. However, other embodiments, such as a fully threaded cortical screw, a partially threaded cortical screw, and a partially threaded axially displaced double-lead threaded screw may be practiced, for example, according to the thread patterns of the screws of FIGS. 25-27 and variations thereof. The screw 360 of FIG. 31 may be used, for example, as a cancellous and cortical screw, for engaging, with its different types of threads over different portions of the length of its shaft, different types of bone, such as cancellous bone and cortical bone. The screw 360 of FIG. 31 comprises a self-drilling tip 361. The self-drilling tip can have a cutting edge 363 and a following edge 365 that define an angular cavity in self-drilling tip 361 that can serve as a straight flute to expose cutting edge 363.

Screw 360 comprises single lead wide pitch thread 370 that begins at thread starting point 377 and continues to thread ending point 386. As thread starting point 377 can lie along cutting edge 363, self-drilling tip 361 can serve as a self-tapping tip as well as a self-drilling tip. Self-drilling tip 361 can both drill a hole for the shaft of screw 360 and cut a helical groove for single lead wide pitch thread 370 to engage. Along a distal portion of the shaft of screw 360, single lead wide pitch thread 370 form a single helix where the pitch is sufficient to accommodate the width of an additional thread of the same pitch between adjacent turns of single lead wide pitch thread 370. However, over the distal portion, the additional thread is absent. Instead, the cylindrically helical unthreaded portion of the shaft exists between adjacent turns of the single lead wide pitch thread 370 over the distal portion of screw 360.

Above the distal portion of screw 360, a thread-cutting edge 373 of additional wide pitch thread 371 lies between adjacent turns of single lead wide pitch thread 370. Additional wide pitch thread 371 forms a helix whose turns lie between the turns of single lead wide pitch thread 370 along the same axis as single lead wide pitch thread 370. Thus, alternations of single lead wide pitch thread 370 and additional wide pitch thread 371 lie along a proximal portion of screw 360 above the distal portion of screw 360. Single lead wide pitch thread 370 continues until thread termination 386. Additional wide pitch thread 371 continues until thread termination 375. In the illustrated embodiment, thread termination 386 and thread termination 375 lie at the same distance along the shaft of screw 360 (e.g., at the same distance from annular ledge 364, and, e.g., at the same distance from self-drilling tip 361).

Proximal to (e.g., above) the proximal portion of the shaft of screw 360 where single lead wide pitch thread 370 and additional wide pitch thread 371 are located, a cylindrical portion 368 of screw 360 may be located. In accordance with other embodiments, cylindrical portion 368 may be omitted. Proximal to (e.g., above) cylindrical portion 368 of screw 360 or the proximal portion of the shaft of screw 360, a transitional portion 387 transitioning to a frustoconical distal portion 353 of a head of screw 360 may be located. Annular boundary 346 lies between cylindrical portion 368 and transition portion 387. Annular boundary 344 lies between transition portion 387 and frustoconical distal portion 353. In accordance with other embodiments, transitional portion 387 may be omitted. Proximal to (e.g., above) transitional portion 387 or cylindrical portion 368 or the proximal portion of the shaft of screw 360, frustoconical distal portion 353 of the head of screw 360 is located. An upper edge of frustoconical distal portion 353 meets lower annular ledge 354 of flange 403. Lower annular ledge extends circularly outward from frustoconical distal portion 353 to a lower circular edge of flange 403. Cylindrical surface 355 of flange 403 extends upward to an upper circular edge of flange 403. Upper annular ledge 364 of flange 403 extends circularly inward from the upper circular edge of flange 403. In the illustrated embodiment, a cylindrical riser 372 lies proximal to (e.g., above) upper annular ledge 364. Thus, an inner circular edge of upper annular ledge 364 meets a lower circular edge of cylindrical riser 372. Cylindrical riser 372 rises to an upper end surface 362. Upper end surface 362 may be planar. A cavity may be defined in upper end surface 362 to accept a screwdriver for driving screw 360 into and out of a material, such as bone. The cavity defined in upper end surface 362 may, for example, be multi-lobular, polygonal, or multi-slotted. Upper annular ledge 364 may be at the same level as upper end surface 362, obviating cylindrical riser 372, or at a more distal level than upper end surface 362 by virtue of the translational displacement along the axis of screw 360 provided by cylindrical riser 372.

As thread starting point 377 forms a single lead and thread starting point 377 and thread cutting edge 373 together form a double lead, screw 360 is a single lead screw along the distal portion of its shaft and is a double lead screw along the proximal portion of its shaft. The single lead wide pitch thread 370 can provide compatibility with less dense materials, such as cancellous bone, while the combination of the single lead wide pitch thread 370 and the additional wide pitch thread 371 can provide compatibility with denser materials, such as cortical bone. Thus, screw 360 can provide cancellous bone and cortical bone compatibility in a single screw. As noted above, other embodiments with other thread configurations can provide a single type of such two types of bone compatibility or other types of bone compatibility.

Figure 32:
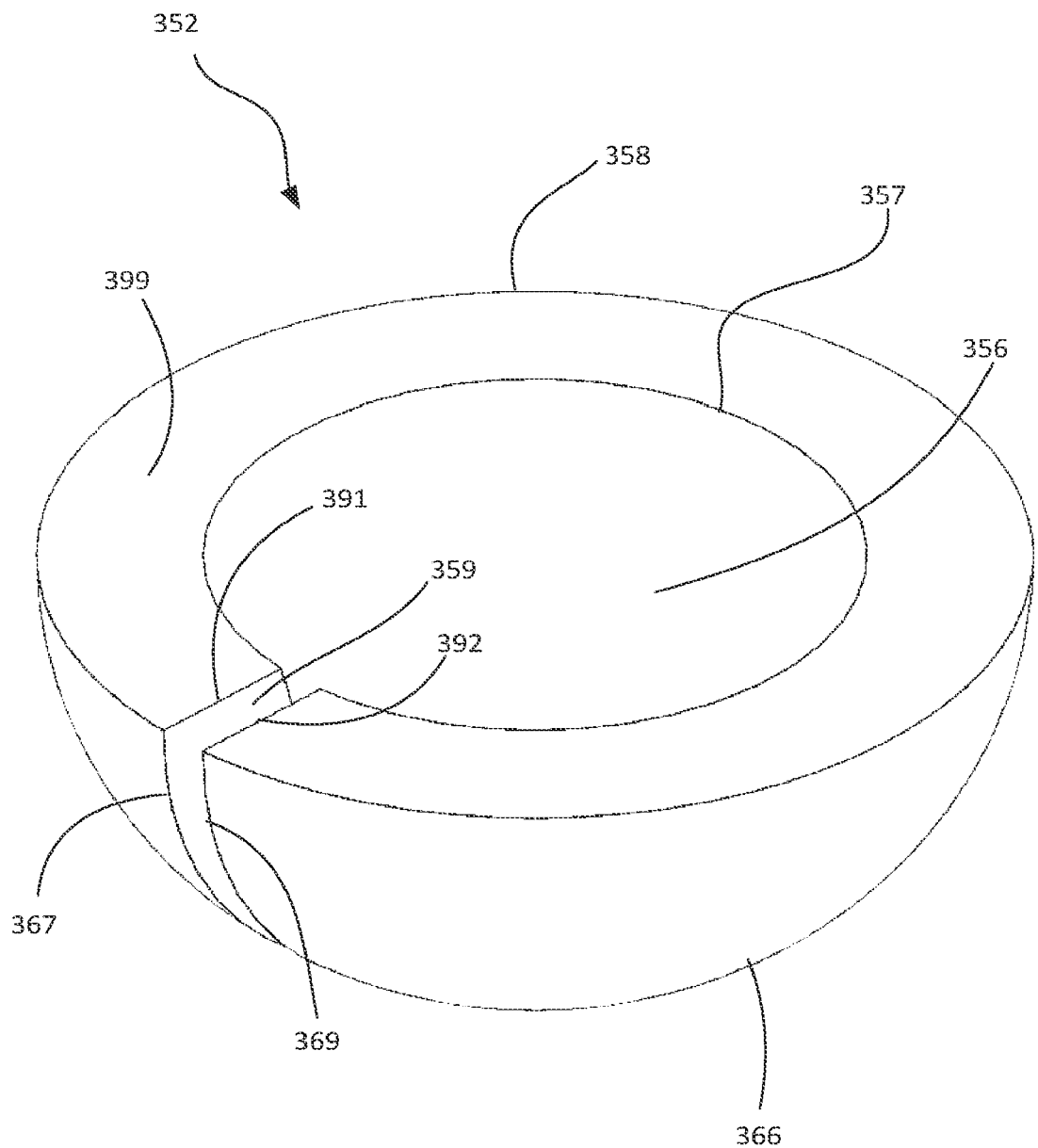
FIG. 32 is a perspective view diagram illustrating a locking ring for a locking screw assembly in accordance with at least one embodiment.

FIG. 32 is a perspective view diagram illustrating a locking ring for a locking screw assembly in accordance with at least one embodiment. Locking ring 352 can have a split ring configuration, wherein gap 359 is defined between substantially radial planar surfaces having proximal edges 391 and 392 and distal edges 367 and 369. Locking ring 352 can have a convexly curved exterior surface 366. The convexly curved exterior surface 366 extends from a annular upper surface 399 at outer circular edge 358 downward to a hole defined in a distal portion of locking ring 352 or, alternatively, to a surface situated between a lower edge of convexly curved exterior surface 366 and the hole defined in the distal portion of locking ring 352. Such a surface may, for example, be a circular flat surface or another type of surface. If such a surface is a circular flat surface, it may, for example, be parallel to annular upper surface 399. According to at least one embodiment, convexly curved exterior surface 366 can be an approximately hemispherical exterior surface. Convexly curved exterior surface 366 can be considered a distal surface relative to the more proximal annular upper surface 399. Convexly curved exterior surface 366 is aligned axially with an axis of locking ring 352.

Annular upper surface 399 may, for example, be a flat annular upper surface. Annular upper surface 399 extends circularly inward from outer circular edge 358 to inner circular edge 357. A frustoconical interior surface 356 of locking ring 352 is aligned axially with the axis of locking ring 352. Frustoconical interior surface 356 defines a frustoconical cavity in locking ring 352. The frustoconical cavity opens into a hole in the distal portion of locking ring 352. The frustoconical cavity is aligned axially with the axis of locking ring 352. The proximal diameter of frustoconical interior surface 356 is larger than the distal diameter of frustoconical interior surface 356.

Figure 33:
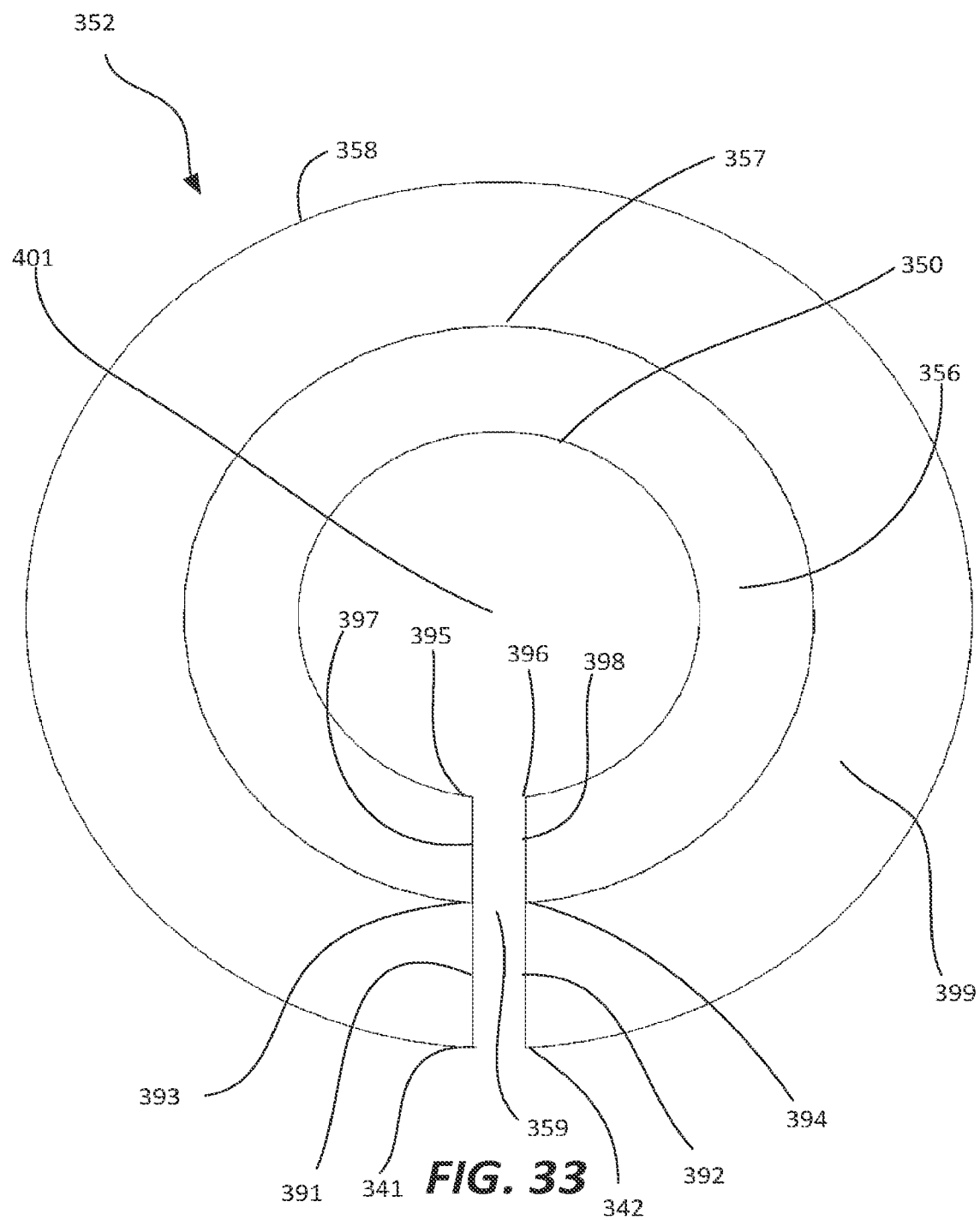
FIG. 33 is a plan view diagram illustrating a locking ring for a locking screw assembly in accordance with at least one embodiment.

FIG. 33 is a plan view diagram illustrating a locking ring for a locking screw assembly in accordance with at least one embodiment. Locking ring 352 has an annular upper surface 399 extending from outer circular edge 358 circularly inward to inner circular edge 357. From inner circular edge 357, frustoconical interior surface 356 extends distally to distal circular edge 350 of frustoconical interior surface 356. Distal circular edge 350 defines the distal edge of a distal axial hole at the distal end of the frustoconical cavity defined in locking ring 352 by frustoconical interior surface 356. The distal axial hole, a proximal axial hole of larger diameter than the distal axial hole, and the frustoconical cavity between the distal axial hole and the proximal axial hole provide a space 401 in which frustoconical distal portion 353 of screw 360 may be inserted. The frustoconical exterior of frustoconical distal portion 353 of screw 360 can engage the frustoconical interior of frustoconical interior surface 356 of locking ring 352. Axial motion of screw 360 relative to locking ring 352 can provide a wedging action to exert force radially against frustoconical interior surface 356 to expand locking ring 352 to lock screw 360 in position relative to a concavely curved cavity in an orthopedic plate in which a screw assembly comprising screw 360 and locking ring 352 are installed.

Locking ring 352 can be of a split ring configuration. Locking ring 352 need not be circularly continuous but can be interrupted by a gap 359 to form a "C" shape, as shown in FIG. 33. Gap 359 may be in the form, for example, of a slit. The slit may, for example, be defined by parallel surfaces. As an example, the surfaces may be substantially radial to an axis of locking ring 352. Alternatively, the slit may be defined with a different orientation, which may, for example, be skewed relative to the axis of locking ring 352. The surfaces that define the slit may, as examples, be planar or non-planar.

In the illustrated example, gap 359 is defined by a first surface having proximal edge 391, from outer proximal corner 341 to inner proximal corner 393, and interior edge 397 from inner proximal corner 393 to inner distal corner 395, and by a second surface having proximal edge 392, from outer proximal corner 342 to inner proximal corner 394, and interior edge 398 from inner proximal corner 394 to inner distal corner 396.

Figure 34:
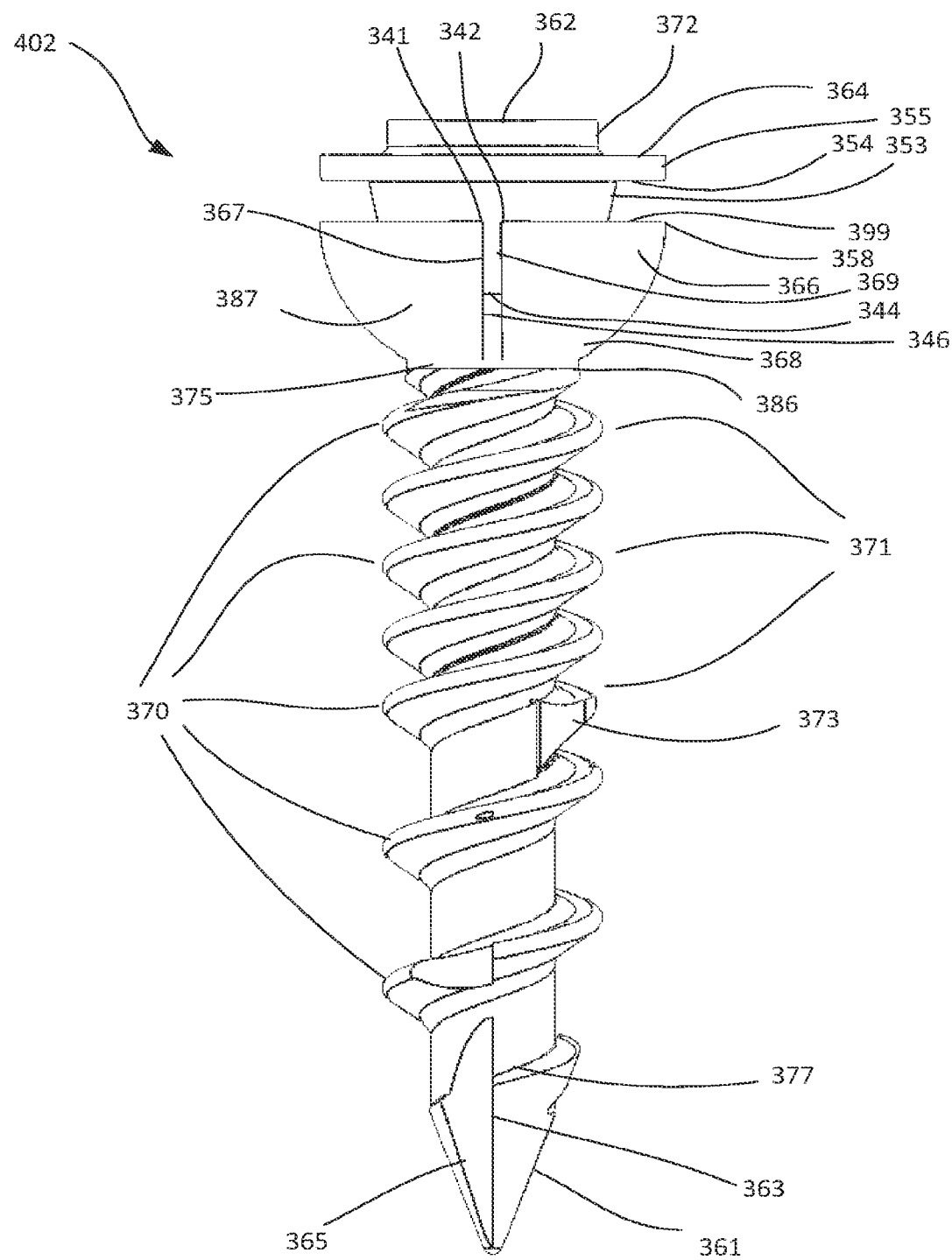
FIG. 34 is an elevation view diagram illustrating a locking screw assembly in an unlocked configuration in accordance with at least one embodiment.

FIG. 34 is an elevation view diagram illustrating a locking screw assembly in an unlocked configuration in accordance with at least one embodiment. Locking screw assembly 402 comprises screw 360 and locking ring 352. As shown in FIG. 34, in an unlocked configuration, locking ring 352 is situated around screw 360 at a more distal position of a range of axial positions. The more distal position minimizes engagement of frustoconical portion 353 of screw 360 with frustoconical interior surface 356 of locking ring 352, maintaining locking ring in a substantially neutral configuration having a relatively smaller diameter. As will be shown in FIG. 35, screw 360 can force locking ring to a more proximal position, whereupon engagement of frustoconical portion 353 of screw 360 with frustoconical interior surface 356 of locking ring applies radially outward force to locking ring 352, expanding locking ring to a forcefully displaced configuration having a relatively larger diameter. As an example, screw 360 and locking ring 352 can be said to telescopingly engage one another.

In the illustrated example, annular gap 404 exists between annular upper surface 399 of locking ring 352 and lower annular ledge 354 of the flange 403 of screw 360. An upper portion of frustoconical portion 353 of screw 360 can be seen through annular gap 404. Annular gap 404 can be configured to be thinner than a thickness of a locking tab, such as locking tabs 124 and 125 of FIG. 28, allowing a locking clip, such as single hole locking clip 203 of FIG. 28 or a multiple hole locking clip to be used with locking screw assembly 402 without the locking tabs getting caught in annular gap 404. A lower portion of frustoconical portion 353 of screw 360 can be seen through an upper portion of gap 359. A portion of annular boundaries 344 and 346, as well as a portion of transition portion 387, of screw 360 can be seen through a central portion of gap 359. A portion of cylindrical portion 368 can be seen through a lower portion of gap 359. As can be seen from the example of FIG. 34, a diameter of outer circular edge 358, when expanded by a wedging action of frustoconical portion 353 of screw 360 against frustoconical interior surface 356 of locking ring 352, can be substantially the same as a diameter of cylindrical surface 355, allowing a smooth transition between the profile of convexly curved exterior surface 366 and the profile of flange 403 when locking screw assembly 402 is in a locked configuration, as will be discussed below in reference to FIG. 35.

Figure 35:
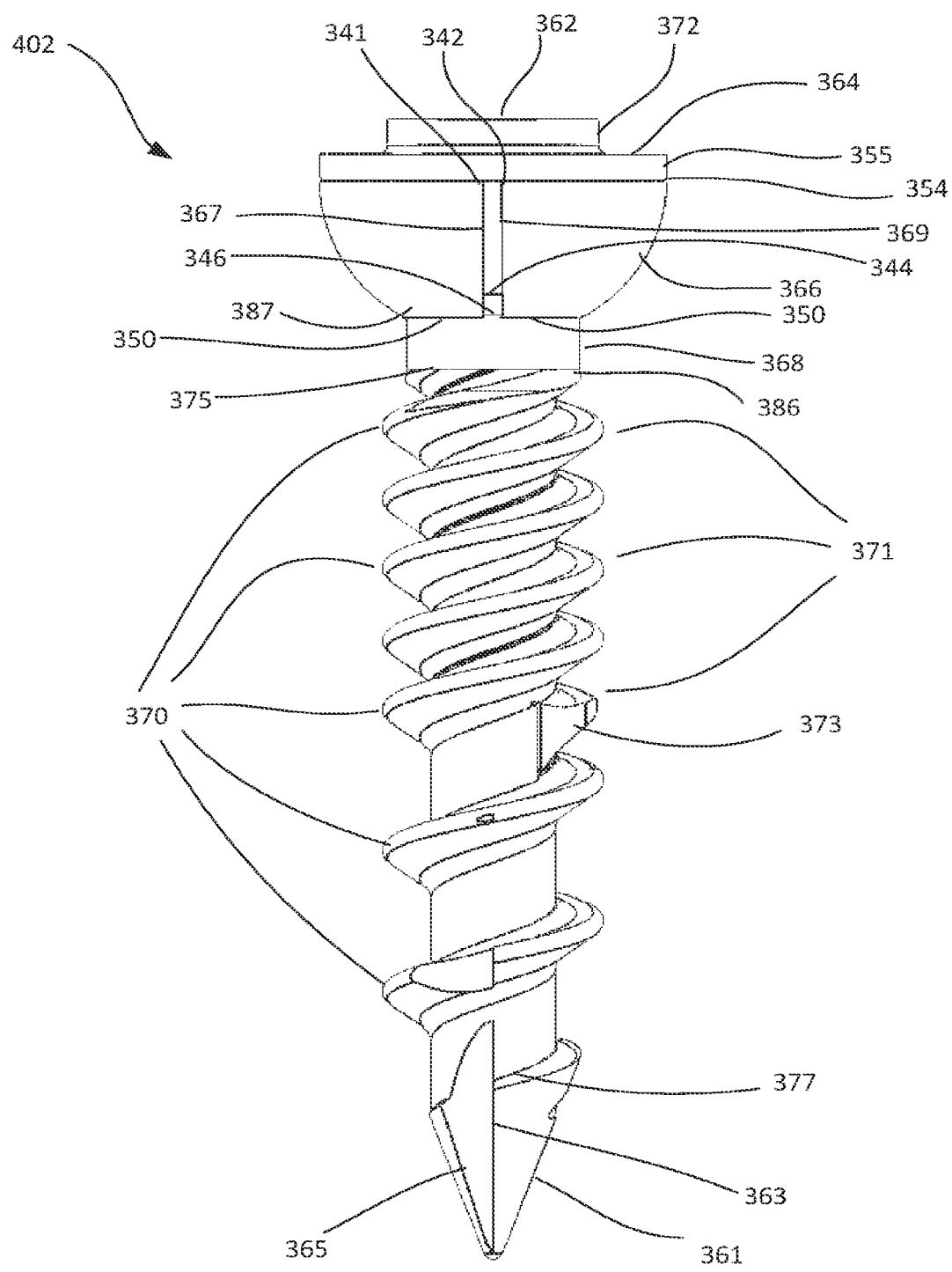
FIG. 35 is a perspective view diagram illustrating a locking screw assembly in a locked configuration in accordance with at least one embodiment.

FIG. 35 is a perspective view diagram illustrating a locking screw assembly in a locked configuration in accordance with at least one embodiment. Locking screw assembly 402 is shown in FIG. 35 with locking ring 352 driven axially upward relative to screw 360 until annular upper surface 399 is near or in contact with lower annular ledge 354 of flange 403 of screw 360. A portion of frustoconical distal portion 353 of screw 360 can be seen through an upper portion of gap 359. A portion of annular boundary 344 and transition portion 387 can be seen through a lower portion of gap 359. The illustrated example of locking ring 352 has a distal circular edge 350 where convexly curved exterior surface 366 meets frustoconical interior surface 356 of locking ring 352. As noted above, in the locked position the diameter of locking ring 352 is expanded to lock locking ring 352 and screw 360 into a concavely curved cavity of an orthopedic plate in which locking screw assembly 402 is installed. An outside diameter of a proximal edge of locking ring 352 can be substantially the same as a diameter of cylindrical surface 355, allowing a smooth transition between the profile of convexly curved exterior surface 366 and the profile of flange 403 when locking screw assembly 402 is in a locked configuration.

Embodiments described herein solve the problem of conventionally designed orthopedic plate and screw systems in which the screws may back out of the bone, thus affecting the stability provided by the orthopedic plate and the healing process. The protrusions on the clamp provide resistance to the orthopedic screw once inserted into the bone to prevent back out. In addition, revising or removing the bone plate can be easier because of the superior visibility and access to engage the orthopedic screws.

In accordance with at least one embodiment, a plate is provided for attachment to a bone, wherein said plate comprises a first surface; a second surface positioned opposite from the first surface; and a plurality of holes extending from the top surface to the second surface through the plate, wherein each hole of the plurality of holes are dimensioned and configured to accommodate an orthopedic screw, each hole comprising a substantially semi-circle-shaped clamp configured with at least one protrusion to cover a portion of a head of the orthopedic screw; and a channel, within which the semi-circle-shaped clamp can be seated. In accordance with at least one embodiment, the plate is curved. In accordance with at least one embodiment, the plate comprises any of a cervical bone plate, an anterior lumbar plate, and a lateral lumbar plate. In accordance with at least one embodiment, each hole of the plurality of holes can be configured with a conical taper.

In accordance with at least one embodiment, a system is provided for attachment to a bone, wherein said system comprises a plate comprises a first surface; a second surface positioned opposite from the first surface; and a plurality of holes extending from the first surface to the second surface through the plate, wherein each hole of the plurality of holes are dimensioned and configured to accommodate an orthopedic screw, each hole comprising a substantially semi-circle-shaped clamp configured with at least one protrusion to cover a portion of a head of the orthopedic screw, where the at least one protrusion has a length extending toward the center of the semi-circle-shaped clamp; and a channel, within which the semi-circle-shaped clamp can be seated; a plurality of orthopedic screws comprising a head; a substantially flat first surface of the head having a first radius; and a substantially flat second surface of the head having a second radius, where the second surface is parallel with the first surface, and the second radius is greater than the first radius and the difference between the first and second radiuses is greater than the length of the at least one protrusion of the semi-circle-shaped clamp. In accordance with at least one embodiment, the plate is curved. In accordance with at least one embodiment, the plate is designed for placement on long bones, the mandible or other portions of the skull, the foot or ankle, the shoulder, the hand or wrist, and along the vertebrae. In accordance with at least one embodiment, each hole of the plurality of holes can be configured with a conical taper. In accordance with at least one embodiment, the plurality of orthopedic screws further comprises a conical taper on the lower end of the head of the screw.

In accordance with at least one embodiment, a method is provided for attaching a plate to a bone, the method comprising a) placing a plate on the bone, the plate comprising a first surface; a second surface positioned opposite from the first surface; and a plurality of holes extending from the first surface to the second surface through the plate, wherein each hole of the plurality of holes are dimensioned and configured to accommodate an orthopedic screw, each hole comprising a substantially semi-circle-shaped clamp configured with at least one protrusion to cover a portion of a head of the orthopedic screw, where the at least one protrusion has a length extending toward the center of the semi-circle-shaped clamp; and a channel, within which the semi-circle-shaped clamp can be seated; b) securing the plate to the bone with a plurality of orthopedic screws placed in at least two of the plurality of holes, with the orthopedic screws comprising a substantially flat first surface having a first radius; and a substantially flat second surface having a second radius, where the second surface is parallel with the first surface, and the second radius is greater than the first radius and the difference between the first and second radiuses is greater than the length of the at least one protrusion of the semi-circle-shaped clamp. In accordance with at least one embodiment, the plate is curved. In accordance with at least one embodiment, the plate is designed for placement on long bones, the mandible or other portions of the skull, the foot or ankle, the shoulder, the hand or wrist, and along the vertebrae. In accordance with at least one embodiment, each hole of the plurality of holes is configured with a conical taper. In accordance with at least one embodiment, step b) further comprises 1) securing the plate to the bone with an orthopedic screw placed in a first hole in the plate that is located at a first longitudinal end of the plate; 2) applying a traction force to a second longitudinal end of the plate opposite of the first longitudinal end; and 3) while still applying the traction force to the second longitudinal end of the plate, further securing the plate to the bone with at least one orthopedic screw placed in the holes of the plate. In accordance with at least one embodiment, step 3) comprises, while still applying the traction force to the second longitudinal end of the plate, further securing the plate to the bone with an orthopedic screw placed in a second hole in the plate that is located at or near the second longitudinal end.

In accordance with at least one embodiment, an orthopedic screw comprises a head; a substantially flat first surface of the head having a first radius; and a substantially flat second surface of the head having a second radius, where the second surface is parallel with the first surface, and the second radius is greater than the first radius. In accordance with at least one embodiment, the orthopedic screw further comprises a conical taper on the lower end of the head of the screw.

In accordance with at least one embodiment, a flexure member of a locking clip lies arcuately peripheral to a fastener head of a fastener which the locking clip is adapted to retain. In accordance with at least one embodiment, the flexure member bears upon the bone fixation plate within a cavity defined in the plate, wherein the flexure member is situated in the cavity. In accordance with at least one embodiment, the flexure member bears upon the bone fixation plate within a cavity defined within the plate, wherein the cavity extends to further define a fastener head cavity in communication with a flexure member cavity. In accordance with at least one embodiment, the flexure member spans an indirect length between two body portions of the locking clip such that deflection of the flexure member from displacement of a first locking tab of a first body portion of the two body portions from its neutral position by a fastener head causes a second locking tab of a second body portion of the two body portions to bear upon the fastener head. The first locking tab and the second locking tab can exert forces in opposite directions. The first locking tab and the second locking tab can engage opposite portions of the fastener head. The opposite portions of the fastener head can, for example, be diametrically opposite. As another example, the opposite portions of the fastener head need not be diametrically opposite.

In accordance with at least one embodiment, a locking fastener assembly comprises a fastener and a locking ring. In accordance with at least one embodiment, the fastener is a screw. In accordance with at least one embodiment, a frustoconical cavity is defined in the locking ring. In accordance with at least one embodiment, a concavely curved cavity is defined in the locking ring. In accordance with at least one embodiment, a convexly curved cavity is defined in the locking ring. In accordance with at least one embodiment, a convex-to-frustoconical transition is defined in the locking ring. In accordance with at least one embodiment, a frustoconical-to-concave transition is defined in the locking ring.

In accordance with at least one embodiment, a full slit is defined in the locking ring, interrupting annular continuity of the locking ring. In accordance with at least one embodiment, a partial slit is defined in the locking ring, interrupting annular continuity of the locking ring over a first portion of the height of the locking ring but maintaining annular continuity of the locking ring over a second portion of the height of the locking ring. In accordance with at least one embodiment, multiple slits are defined in the locking ring. In accordance with at least one embodiment, a first subset of the multiple slits comprises at least one full slit and a second subset of the multiple slits comprises at least one partial slit. In accordance with at least one embodiment, at least one upper partial slit begins at a top edge of the locking ring but does not continue to a bottom edge of the locking ring. In accordance with at least one embodiment, at least one lower partial slit begins at a bottom edge of the locking ring but does not continue to a top edge of the locking ring. In accordance with at least one embodiment, the locking ring defines at least one upper partial slit and at least one lower partial slit. In accordance with at least one embodiment, the locking ring defines at least two upper partial slits. In accordance with at least one embodiment, the locking ring defines at least two lower partial slits. In accordance with at least one embodiment, the locking ring defines at least four alternating upper and lower partial slits.

In accordance with at least one embodiment, a fastener exterior grip surface is provided on an exterior fastener surface of a fastener, for example, on a wedging portion of the fastener for engagement with an locking ring interior surface of a locking ring. In accordance with at least one embodiment, a locking ring interior grip surface is provided on a locking ring interior surface of a locking ring, for example, on a locking ring interior surface for engagement with a fastener exterior surface of a fastener. In accordance with at least one embodiment, a locking ring exterior grip surface is provided on a locking ring exterior surface of a locking ring, for example, on a locking ring exterior surface for engagement with a bone fixation plate cavity surface of a bone fixation plate. In accordance with at least one embodiment, a bone fixation plate cavity grip surface is provided on a bone fixation plate cavity surface of a bone fixation plate for engagement with a locking ring exterior surface of a locking ring. Any or all of the foregoing grip surfaces may be provided alone, or multiple ones of the foregoing grip surfaces may be provided. For example, a fastener exterior grip surface and a locking ring interior grip surface may be provided to interact with each other. Such interaction may, for example, provide that rotation of the fastener, such as via a screwdriver, results in rotation in unison of both the fastener and the locking ring. Examples of grip surfaces include a machined surface, such as on comprising stipples, ridges, channels, serrations, or knurling; a particulate blasted surface; an acid etched surface; a laser formed surface; a laser resurfaced surface; a thermal spray formed surface; a hydroxylapatite (HA) coated surface; or combinations thereof. Surfaces not intended to serve as grip surfaces may be, for example, naturally or synthetically oxidized surfaces, anodized surfaces, polymer-coated surfaces, or combinations thereof.

While embodiments are described with respect to particular types of fasteners, such as screws having particular types of tips and threads, other embodiments may be practiced with other types of tips and threads. For example, fasteners may be practiced with self-drilling tips which also provide self-tapping of threads, self-tapping threads that do not provide self-drilling, or smoothly curved tips that need not provide either self-drilling or self-tapping.

In accordance with at least one embodiment, a fastener for a locking fastener assembly, such as a locking screw assembly, can include a flange adjacent to a wedging surface of a wedging portion of the locking fastener. The flange can have a radially greater extent than the wedging surface. The flange can serve as a travel stop to limit the axial travel of a locking ring of the locking fastener assembly. By limiting the axial travel of the locking ring relative to the locking fastener, the extent of the wedging action can be limited, limiting the extent to which the locking ring can be expanded according to the wedging action. Thus, overexpansion of the locking ring can be prevented.

In accordance with at least one embodiment, the locking ring has a locking ring convexly curved exterior surface and a locking ring interior surface configured to cooperate with a wedging portion of a fastener exterior surface. In accordance with at least one embodiment, the locking ring convexly curved exterior surface meets the locking ring interior surface at a locking ring lower annular boundary of the locking ring. In accordance with at least one embodiment, a locking ring lower annular surface lies between the lowest extent of the locking ring convexly curved exterior surface and the lowest extent of the locking ring interior surface. The locking ring lower annular surface may, for example, be a planar locking ring lower annular surface or a frustoconical locking ring lower annular surface.

In accordance with at least one embodiment, the locking ring has a locking ring upper annular surface disposed between the highest extent of the locking ring convexly curved exterior surface and the highest extent of the locking ring interior surface. The locking ring upper annular surface may, for example, be a planar locking ring upper annular surface or a frustoconical locking ring upper annular surface.

In accordance with at least one embodiment, manufacturing of such embodiment may be performed using known manufacturing techniques, which may include, for example, milling, such as with a computer numerically controlled (CNC) mill; turning, such as with a CNC lathe; electrical discharge machining (EDM); laser sintering; particulate blasting; acid etching; anodizing; laser marking; and combinations thereof. Alternatively or in conjunction with one or more such manufacturing techniques, other known techniques may be used.

Articles in accordance with at least one embodiment may be formed from a biocompatible material substantially consisting of titanium (Ti). Articles in accordance with at least one embodiment may be formed from biocompatible metallic materials substantially consisting primarily of titanium (Ti) alloyed with at least one of aluminum (Al), vanadium (V), zirconium (Zr), manganese (Mn), molybdenum (Mo), chromium (Cr), tin (Sn), palladium (Pd), nickel (Ni), silicon (Si), iron (Fe), copper (Cu), niobium (Nb), boron (B), cobalt (Co), ruthenium (Ru), tantalum (Ta), and indium (In). As examples, embodiments, including embodiments of a locking clip, a bone fixation plate, a screw, and a locking ring, may be formed from one or more materials selected from a group consisting of nitinol, titanium, and stainless steel.

At least one embodiment may be used for a human orthopedic application to provide bone fixation for a human. At least one embodiment may be used for a veterinary application to provide bone fixation for an animal.

In accordance with at least one embodiment, a locking clip can be formed as a separate structure from a bone fixation plate and installed in the bone fixation plate. In accordance with at least one embodiment, the neutral (e.g., unbiased) shape of the locking clip is configured to be securely retained in the bone fixation plate, preventing the locking clip from unintentionally being removed from the bone fixation plate. As an example, the locking clip can be configured to require a clip tool be used to forcibly flex the locking clip into a shape that allows removal of the locking clip from the bone fixation plate when removal is desired. Accordingly to at least one embodiment, the clip tool can be used to forcibly flex the locking clip in a manner (e.g., a translating but non-rotating manner) to remove a fastener from the bone fixation plate without removing the locking clip from the bone fixation plate.

In accordance with at least one embodiment, a locking clip is formed integrally with the bone fixation plate. As an example, an additive manufacturing technique can be used to construct the bone fixation plate and at least one locking clip as an integral structure within a single piece of material. As another example, a subtractive manufacturing technique can be used to remove material so as to form at least one locking clip as an integral structure within a single piece of material that also forms the bone fixation plate. As another example, subtractive and additive manufacturing techniques can be used together to produce at least one locking clip as an integral structure within a single piece of material that also forms the bone fixation plate.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

Although the invention is described herein with reference to specific embodiments, various modifications and changes can be made without departing from the scope of the present invention, as set forth in the claims below. Accordingly, the specification and figures are to be regarded in an illustrative rather than a restrictive sense, and all such modifications are intended to be included within the scope of the present invention. Any benefits, advantages, or solutions to problems that are described herein with regard to specific embodiments are not intended to be construed as a critical, required, or essential feature or element of any or all the claims.

Unless stated otherwise, terms such as "first" and "second" are used to arbitrarily distinguish between the elements such terms describe. Thus, these terms are not necessarily intended to indicate temporal or other prioritization of such elements. The terms "a" and "an" are defined as one or more unless stated otherwise. The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system, device, or apparatus that "comprises," "has," "includes" or "contains" one or more elements possesses those one or more elements but is not limited to possessing only those one or more elements. Similarly, a method or process that "comprises." "has." "includes" or "contains" one or more operations possesses those one or more operations but is not limited to possessing only those one or more operations.

What is claimed is:

1. A bone fixation plate assembly, comprising:
   a bone fixation plate including a fastener hole and a clip cavity adjacent to the fastener hole; and
   a locking clip comprising:
      a flexure member and situated at least in part in the clip cavity; and
      a locking tab having a convex shape extending inward relative to the flexure member;
   wherein the flexure member is resiliently flexible to permit displacement of the locking tab to allow passage of a fastener head of a fastener; and
   wherein the locking tab is configured to provide an axial limitation to motion of the fastener in a non-rotationally-ratcheting manner.

2. The bone fixation plate assembly of claim 1, wherein a spring tension of the flexure member in a displaced state biases the locking tab to return to a neutral position once the fastener head has passed below an underside surface of the locking tab.

3. The bone fixation plate assembly of claim 1, wherein the fastener hole includes a bottom taper configured to receive a tapered surface of a head of a fastener at either of an angled and a perpendicular approach relative to the bone fixation plate.

4. The bone fixation plate assembly of claim 1, wherein the clip cavity is radially oriented to correspond to a partial circular shape of the flexure member.

5. The bone fixation plate assembly of claim 1, the clip cavity is sized to allow flex of the flexure member within the clip cavity when the flexure member is in a displaced state.

6. A bone fixation plate assembly, comprising:
   a bone fixation plate comprising:
      a fastener hole; and a clip cavity located adjacent to the fastener hole; and a locking clip comprising:

a flexure member situated at least in part in the clip cavity; and a locking tab having a convex shape extending inward toward a center of the fastener hole;

wherein the flexure member is resiliently flexible to permit displacement of the locking tab to allow passage of a fastener head of a fastener; and wherein the locking tab is configured to provide an axial limitation to motion of the fastener in a non-rotationally-ratcheting manner.

7. The bone fixation plate assembly of claim 6, wherein a spring tension of the flexure member in a displaced state biases the locking tab to return to a neutral position once the fastener head has passed below an underside surface of the locking tab.

8. The bone fixation plate assembly of claim 6, the clip cavity is radially oriented around at least a portion of the fastener hole.

9. The bone fixation plate assembly of claim 6, wherein the fastener hole includes a bottom taper configured to receive a tapered surface of a head of a fastener at either of an angled and a perpendicular approach relative to the bone fixation plate.

10. The bone fixation plate assembly of claim 6, wherein the clip cavity is sized to allow flex of the flexure member within the clip cavity when the flexure member is in a displaced state.

11. A bone fixation plate assembly, comprising:

a bone fixation plate comprising:

a fastener hole; and a clip cavity located adjacent to the fastener hole; and a locking clip comprising:

a flexure member situated at least in part in the clip cavity; and a plurality of locking tabs each having a convex shape extending inward toward a center of the fastener hole;

wherein the flexure member is resiliently flexible to permit displacement of the locking tab to allow passage of a fastener head of a fastener; and wherein the locking tab is configured to provide an axial limitation to motion of the fastener in a non-rotationally-ratcheting manner.

12. The bone fixation plate assembly of claim 11, wherein a spring tension of the flexure member in a displaced state biases the at least one of the two locking tabs to return to a neutral position once the fastener head has passed below an underside surface of the locking tab.

13. The bone fixation plate assembly of claim 11, wherein the fastener hole includes a bottom taper configured to receive a tapered surface of a head of a fastener at either of an angled and a perpendicular approach relative to the bone fixation plate.

14. The bone fixation plate assembly of claim 11, wherein the clip cavity is radially oriented to correspond to a partial circular shape of the flexure member.

15. The bone fixation plate assembly of claim 11, wherein the clip cavity is sized to allow flex of the flexure member within the clip cavity when the flexure member is in a displaced state.

* * * * *